(12) United States Patent
van der Weide et al.

(10) Patent No.: US 9,987,097 B2
(45) Date of Patent: Jun. 5, 2018

(54) SIGNAL TAG DETECTION COMPONENTS, DEVICES, AND SYSTEMS

(71) Applicant: Elucent Medical, Inc., Brookfield, WI (US)

(72) Inventors: Daniel W. van der Weide, Madison, WI (US); Noah van der Weide, Madison, WI (US); Eric N. Rudie, Madison, WI (US); David Miel, Madison, WI (US)

(73) Assignee: Elucent Medical, Inc., Brookfield, WI (US)

( * ) Notice: Subject to any disclaimer, the term of this patent is extended or adjusted under 35 U.S.C. 154(b) by 0 days. days.

(21) Appl. No.: 15/281,862

(22) Filed: Sep. 30, 2016

(65) Prior Publication Data

US 2017/0095315 A1      Apr. 6, 2017

Related U.S. Application Data

(63) Continuation-in-part of application No. 14/992,443, filed on Jan. 11, 2016.
(Continued)

(51) Int. Cl.
*A61B 90/90* (2016.01)
*A61B 90/00* (2016.01)
(Continued)

(52) U.S. Cl.
CPC .............. *A61B 90/39* (2016.02); *A61B 90/98* (2016.02); *A61B 18/14* (2013.01);
(Continued)

(58) Field of Classification Search
CPC ........... A61B 34/73; A61B 34/20; A61B 5/06; A61B 90/39; A61B 1/00158;
(Continued)

(56) References Cited

U.S. PATENT DOCUMENTS 3,689,885 A     9/1972 Kaplan et al.
3,706,094 A     12/1972 Cole et al.
(Continued)

FOREIGN PATENT DOCUMENTS

WO     WO 2015112863        1/2016

OTHER PUBLICATIONS

Li et al., Radio frequency identification technology: applications, technical challenges and strategies, Management Department Journal Article, 2006, paper 34, 28 pages.
(Continued)

*Primary Examiner* — Christine H Matthews
(74) *Attorney, Agent, or Firm* — Casimir Jones, S.C.

(57) ABSTRACT

Provided herein are systems, devices, assemblies, and methods for localization of a tag in a tissue of a patient. For example, provided herein are systems, devices, and methods employing an implantable tag that emits sidebands at defined frequencies upon activation by a magnetic field generated by a remote activating device, and a plurality of witness stations configured to detect such sidebands. Also provided herein are herein are systems, devices, and methods employing a detection component that is attached to or integrated with a surgical device.

23 Claims, 13 Drawing Sheets

Related U.S. Application Data

(60) Provisional application No. 62/236,660, filed on Oct. 2, 2015, provisional application No. 62/374,402, filed on Aug. 12, 2016.

(51) Int. Cl.
  *A61B 90/98* (2016.01)
  *A61B 18/14* (2006.01)

(52) U.S. Cl.
  CPC ............... *A61B 2090/3945* (2016.02); *A61B 2090/3958* (2016.02); *A61B 2562/0223* (2013.01)

(58) Field of Classification Search
  CPC ............ A61B 2034/2051; A61B 5/062; A61B 2017/00876; A61B 5/073; A61B 90/98
  See application file for complete search history.

(56) References Cited

U.S. PATENT DOCUMENTS

| | | |
|---|---|---|
| 4,494,545 A | 1/1985 | Slocum et al. |
| 4,561,443 A | 12/1985 | Hogrefe et al. |
| 4,804,054 A | 2/1989 | Howson et al. |
| 5,012,236 A | 4/1991 | Troyk et al. |
| 5,095,309 A | 3/1992 | Troyk et al. |
| 5,198,807 A | 3/1993 | Troyk et al. |
| 5,241,961 A | 9/1993 | Henry |
| 6,047,214 A | 4/2000 | Mueller et al. |
| 6,053,873 A | 4/2000 | Govari et al. |
| 6,249,212 B1 | 6/2001 | Beigel et al. |
| 6,263,247 B1 | 7/2001 | Mueller et al. |
| 6,361,532 B1 | 3/2002 | Burek |
| 6,499,488 B1 | 12/2002 | Hunter et al. |
| 6,765,476 B2 | 7/2004 | Steele et al. |
| 6,784,788 B2 | 8/2004 | Beigel et al. |
| 7,007,699 B2 | 3/2006 | Martinelli et al. |
| 7,174,201 B2 | 2/2007 | Govari et al. |
| 7,307,530 B2 | 12/2007 | Fabian et al. |
| 7,319,396 B2 | 1/2008 | Homanfar et al. |
| 7,347,379 B2 | 3/2008 | Ward et al. |
| 7,366,562 B2 | 4/2008 | Dukesherer et al. |
| 7,411,505 B2 | 8/2008 | Smith et al. |
| 7,414,404 B2 | 8/2008 | Keene |
| 7,420,468 B2 | 9/2008 | Fabian et al. |
| 7,474,223 B2 | 1/2009 | Nycz et al. |
| 7,518,518 B2 | 4/2009 | Homanfar et al. |
| 7,549,960 B2 | 6/2009 | Govari |
| 7,558,616 B2 | 7/2009 | Govari et al. |
| 7,575,550 B1 | 8/2009 | Govari |
| 7,590,441 B2 | 9/2009 | Govari et al. |
| 7,632,270 B2 | 12/2009 | Livneh |
| 7,715,898 B2 | 5/2010 | Anderson |
| 7,751,865 B2 | 7/2010 | Jascob et al. |
| 7,814,916 B2 | 10/2010 | Revie et al. |
| 7,817,040 B2 | 10/2010 | Homanfar et al. |
| 7,818,044 B2 | 10/2010 | Dukesherer et al. |
| 7,840,253 B2 | 11/2010 | Tremblay et al. |
| 7,848,553 B2 | 12/2010 | Hertel et al. |
| 7,871,423 B2 | 1/2011 | Livneh |
| 7,971,341 B2 | 7/2011 | Dukesherer et al. |
| 7,993,335 B2 | 8/2011 | Rioux et al. |
| 8,012,154 B2 | 9/2011 | Livneh |
| 8,057,407 B2 | 11/2011 | Martinelli et al. |
| 8,057,468 B2 | 11/2011 | Konesky |
| 8,100,897 B2 | 1/2012 | Zoran |
| 8,113,210 B2 | 2/2012 | Petcavich et al. |
| 8,114,181 B2 | 2/2012 | Gogolin |
| 8,226,640 B2 | 7/2012 | Zoran |
| 8,239,001 B2 | 8/2012 | Verard et al. |
| 8,271,069 B2 | 9/2012 | Jascob et al. |
| 8,354,837 B2 | 1/2013 | Anderson |
| 8,359,730 B2 | 1/2013 | Burg et al. |
| 8,377,388 B2 | 2/2013 | Konesky |
| 8,409,190 B2 | 4/2013 | Konesky et al. |
| 8,467,852 B2 | 6/2013 | Csavoy et al. |
| 8,549,732 B2 | 10/2013 | Burg et al. |
| 8,628,524 B2 | 1/2014 | Shilev |
| 8,644,907 B2 | 2/2014 | Hartmann et al. |
| 8,647,342 B2 | 2/2014 | Livneh |
| 8,696,663 B2 | 4/2014 | Pardoll et al. |
| 8,728,076 B2 | 5/2014 | Livneh |
| 8,795,265 B2 | 8/2014 | Konesky et al. |
| 8,795,272 B2 | 8/2014 | Rioux et al. |
| 8,802,022 B2 | 8/2014 | Konesky |
| 8,830,037 B2 | 9/2014 | Burke et al. |
| 8,892,185 B2 | 11/2014 | Chi Sing et al. |
| 8,939,153 B1 | 1/2015 | Reicher et al. |
| 8,968,171 B2 | 3/2015 | McKenna et al. |
| 8,973,584 B2 | 3/2015 | Brander et al. |
| 8,979,834 B2 | 3/2015 | Zoran et al. |
| 8,998,899 B2 | 4/2015 | Shilev et al. |
| 9,060,765 B2 | 6/2015 | Rencher et al. |
| 9,095,333 B2 | 8/2015 | Konesky et al. |
| 9,144,453 B2 | 9/2015 | Rencher et al. |
| 9,234,877 B2 | 1/2016 | Hattersley et al. |
| 9,239,314 B2 | 1/2016 | Hattersley et al. |
| 2003/0117269 A1 | 6/2003 | Dimmer |
| 2003/0153850 A1 | 8/2003 | Davis et al. |
| 2004/0199067 A1* | 10/2004 | Bock ............... G01R 33/287 600/411 |
| 2006/0093089 A1* | 5/2006 | Vertatschitsch ...... A61N 5/1049 378/65 |
| 2008/0125630 A1 | 5/2008 | Caylor |
| 2008/0194912 A1 | 8/2008 | Trovato et al. |
| 2008/0213382 A1 | 9/2008 | Ivkov et al. |
| 2008/0281190 A1 | 11/2008 | Petcavich et al. |
| 2009/0281419 A1 | 11/2009 | Troesken et al. |
| 2010/0004523 A1 | 1/2010 | August et al. |
| 2010/0275934 A1 | 11/2010 | Keren |
| 2011/0152673 A1* | 6/2011 | Doerr ............... A61N 1/3718 600/421 |
| 2011/0152677 A1 | 6/2011 | Faul |
| 2011/0201923 A1 | 8/2011 | Shen |
| 2011/0278948 A1 | 11/2011 | Forsell |
| 2012/0082342 A1 | 4/2012 | Kim et al. |
| 2013/0345561 A1 | 12/2013 | Quigley |
| 2014/0018663 A1 | 1/2014 | Harmer et al. |
| 2014/0062717 A1 | 3/2014 | Mudumbai et al. |
| 2014/0066754 A1 | 3/2014 | Chi Sing et al. |
| 2014/0148692 A1 | 5/2014 | Hartmann et al. |
| 2014/0309522 A1 | 10/2014 | Fullerton et al. |
| 2015/0100109 A1 | 4/2015 | Feldman et al. |
| 2015/0129664 A1 | 5/2015 | Brar |
| 2015/0264891 A1 | 9/2015 | Brander et al. |
| 2016/0022216 A1 | 1/2016 | Goldshtein et al. |
| 2016/0051164 A1 | 2/2016 | Derichs et al. |

OTHER PUBLICATIONS

Luini et al., Comparison of Radioguided excision with wire localization of occult breast lesions, Br. J. Surg, 1999, 86:522-525.
Mickle et al., Intellecutual Property and Ubiquitos RFID, Recent Patents on Electrical Engineering, 2008, 1:59-67.
Radio Frequency Identification: Opportunities and Challenges in Implementation, Department of Commerce, 2005, Washington D.C., 38 pages.
Shah et al, Expanding the use of real-time electromagnetic tracking in radiation oncology, J Appl Clin Med Phys. Nov. 15, 2011; 12(4):3590.
Soon, Radio Frequency Identification History and Development, Chapt. 1, Ubiquitous and Pervasive Computing: Concepts, Methodologies, Tools, and Applications, 2010, ed. Symonds, 17 pages.
Stockman, Communication by Means of Reflected Power, Proceedings of the I.R.E., 1948, 36(10):1196-1204.
Takahata et al., Thoracoscopic surgery support system using passive RFID marker, 34th Annual International Conference of the IEEE EMBS, San Diego, CA, Aug. 28-Sep. 1, 2012, pp. 183-186.
Van Lieshout et al., RFID Technologies: Emerging Issues, Challenges and Policy Options, JRC Scientific and Technical Reports, 2007, 278 pages.

(56) References Cited

OTHER PUBLICATIONS

Want, RFID: A Key to Automating Everything, Scientific American, Inc., Jan. 2004, pp. 56-63.
International Search Report and Written Opinion, dated May 5, 2016, for PCT/US2015/012687, 11 pages.

* cited by examiner

SIGNAL TAG DETECTION COMPONENTS, DEVICES, AND SYSTEMS

The present application claims priority to U.S. provisional application Ser. No. 62/236,660, filed Oct. 2, 2015, which is herein incorporated by reference in its entirety. The present application is a continuation-in-part of U.S. application Ser. No. 14/992,443, filed Jan. 11, 2016, which claims priority to U.S. Provisional Application Ser. No. 62/236,660, filed Oct. 2, 2015, both of which are herein incorporated by reference in their entireties. The present application also claims priority to U.S. Provisional Application Ser. No. 62/374,402, filed Aug. 12, 2016, which is herein incorporated by reference in its entirety.

FIELD

Provided herein are systems, devices, assemblies, and methods for localization of a tag in a tissue of a patient. For example, provided herein are systems, devices, and methods employing an implantable tag that emits sidebands at defined frequencies upon activation by a magnetic field generated by a remote activating device, and a plurality of witness stations configured to detect such sidebands. Also provided herein are herein are systems, devices, and methods employing a detection component that is attached to or integrated with a surgical device.

BACKGROUND

A common and serious challenge for many medical procedures is the accurate localization of treatment areas. For example, the location of lesions, such as tumors that are to undergo treatment, including surgical resection, continues to present a challenge to the medical community. Existing systems are expensive, complex, time-consuming, and often unpleasant for the patient. Such issues are illustrated by the surgical treatment of breast lesions.

A common technique used in breast tumor surgery is wire localization of the lesions. Precise preoperative localization of some breast lesions is necessary before removal of the lesion. Wire localization is used to mark the location of a breast abnormality. The procedure ensures greater accuracy for a breast biopsy or lumpectomy. The surgeon typically uses the wire as a guide to the tissue that needs to be removed. Wire localization is typically conducted in the radiology department of the hospital or surgical center. Mammograms (or in some cases, ultrasound images) are taken to show the location of the breast abnormality. Patients are awake during the placement of the wire, but the breast tissue is numbed to reduce or avoid pain from the needle or the wire. It is possible to feel pressure or pulling sensations during the wire placement. Once images have been taken, and the tissue has been numbed, the radiologist will use a needle to target the breast abnormality. The tip of this needle rests in the location that the surgeon needs to find in order to remove the right tissue. A slender wire is threaded down through the needle and out of its tip, to lodge at the target tissue. The needle is removed, leaving the wire in place. With the wire in place, the patient has another mammogram, to check that the tip of the wire is properly positioned. If the wire is not in the correct place, the radiologist will reposition and re-check it, to ensure accurate placement. When the wire is finally positioned, it will be secured in place with tape or a bandage. The wire localization procedure can take about an hour, and is usually scheduled hours before biopsy or lumpectomy. Thus, the patient must often wait hours for surgery with the wire present in their body and protruding from their skin. The wire is removed, along with some breast tissue, during surgery. This process takes many hours, involves multiple imaging steps, and is inconvenient and unpleasant for the patient—as well as being expensive.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is placed in or around the nodule in an attempt to improve localization prior to removal. This procedure usually takes place in the CT suite prior to the removal of the nodule. The patient is then transported to the surgical unit and the surgeon cuts down on the wire, uses a radionuclide detector, or uses visual landmarks to localize and remove the nodule.

In other types of surgeries and medical procedures, physicians may have trouble locating a target prior to removal or manipulation. Examples of this include the removal of masses, fluid collections, foreign bodies or diseased tissues. Other times, placements of catheters or other percutaneous procedures are performed either without direct visualization or with the lack of a specific guidance modality. Performing procedures without precise guidance can increase the amount of damage to normal tissues and decrease the patient's functional status.

Percutaneous biopsy is a well-accepted, safe procedure performed in virtually every hospital. Biopsy often entails placement of a co-axial guide needle through which the biopsy device is placed into the target. Many of the lesions that are removed, punctured or manipulated as described above have previously undergone successful percutaneous biopsy. The placement of the guide needle for biopsy is an opportunity to place a fiduciary or other localizing system without causing additional tissue trauma than the patient would otherwise undergo.

Many other medical devices and procedures could benefit from improved tissue localization. These include any procedure or test that is degraded by any bodily motion such as cardiac motion, respiratory motion, motion produced by the musculoskeletal system, or gastrointestinal/genitourinary motion. Examples of these include external beam radiation therapy, placement of brachytherapy seeds, imaging tests including but not limited to CT, MRI, fluoroscopy, ultrasound, and nuclear medicine, biopsies performed in any fashion, endoscopy, laparoscopic and thoracoscopic surgery and open surgical procedures.

Improved systems and methods are needed for tissue localization for medical procedures.

SUMMARY

Provided herein are systems, devices, assemblies, and methods for localization of one or more tags in a patient (e.g., in a tissue of a patient). For example, provided herein are systems, devices, and methods employing an implantable tag that emits sidebands at defined frequencies upon activation by a magnetic field generated by a remote activating device, and a plurality of witness stations configured to detect such sidebands. Also provided herein are herein are systems, devices, and methods employing a detection component that is attached to or integrated with a surgical device. The systems, devices, assemblies, and method find use in non-medical settings as well.

In some embodiments, the systems and methods comprise a plurality of components. In some embodiments, a first component comprises one or more tags (which may be used interchangeably with the term "marker") whose location, position, distance, or other properties are to be assessed. In some embodiments, the tags are configured to be positioned in a subject at a surgical location or other clinically relevant location to mark a target region within a body. In some embodiments, a second component comprises a remote activating device that generates a magnetic field. In some embodiments, the second component is located in a device positioned near (e.g., below) a subject containing the one or more tags. In some embodiments, the third component comprises a plurality of witness stations configured to receive a signal generated by the one or more tags upon being exposed to the magnetic field generated by the second component. In some embodiments, the second and third components are physically contained in the same device. In some embodiments, a fourth component comprises a medical device location emitter. The fourth component can be integrated into a medical device or attached or otherwise associated with a medical device. The fourth component comprises one or more emitters (e.g., antennas that emit signals or other types of emitters) that generate signals upon exposure to the magnetic field generated by the second component, said signals detectable by the third component. In some embodiments, a fifth component comprises a computing device comprising a processor that receives information from the witness stations of the third component and generates information about the relative locations, distances, or other characteristics of the tags, the medical device, and the witness stations. In some embodiments, the fifth component comprises a display that displays such generated information to a user of the system.

In some embodiments, the first component is a single tag. In some embodiments, it is two or more tags (e.g., 3, 4, 5, 6, 7, 8, 9, 10, 11, 12, etc.). In some embodiments, where more than one tag is employed, the tags are of identical type while in other embodiments they are of a different type.

In some embodiments, the tag comprises a ferrite-core coil antenna (e.g., resonant at 100-200 kHz) coupled to an integrated circuit (IC), which is powered by an AC magnetic field at resonance. In some embodiments, the core is contained in an enclosure (e.g., a cylindrical glass or plastic housing). The AC magnetic field originates from the second component. The exciter antenna(s) is/are driven by a conventional oscillator and power amplifier at a level sufficient to power the tag(s). In some embodiments, the implanted tag amplitude-modulates (AM's) the continuous wave (CW) carrier power from the exciter, thus emitting sidebands at frequencies defined by a number programmed into the tag's counter. In some embodiments, these sidebands, as well as the much stronger CW carrier, are ultimately detected by the third component.

In some embodiments, the tag comprises a self-resonant object (e.g., a small ferrite core with a wound inductor). The wound inductor possesses inter-winding capacitance that in combination with the inductance produces a high frequency resonant circuit. In some embodiments, the tag comprises a resonant object (e.g., the self-resonant object is equipped with a chip capacitor to produce resonance at a prescribed frequency). In some embodiments, the tag comprises a resonant or self-resonant object with a diode. A diode in combination with an LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). In some embodiments, detection occurs similar to a full duplex (FDX) radio frequency identification (RFID) except that the modulation pattern is a simple sub-harmonic rather than a coded binary pattern; in some embodiments, the detection occurs after excitation similar to a half-duplex (HDX) mode of operation.

In some embodiments, the tag is configured for single-use. In some such embodiments, a tag can be disabled or deactivated (e.g., like an EAS tag). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the tag has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.).

In some embodiments, the tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the tag in place, avoiding migration in tissue. These struts may deploy upon placement in tissue. In some embodiments the fastener may be a biocompatible material that bonds with surrounding tissue.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.).

In some embodiments, the tag does not comprise any power source. For example, in some embodiments, the signal is generated from the signal source in response to a magnetic field as the activation event (i.e., electromagnetic induction).

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the second component (or other device) and then acts as a passive transponder to emit microwaves or UHF radio waves. In some embodiments, the RFID chip is read-only. In other embodiments, it is read/write.

The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (e.g., after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, the second component provides a remote activating device having an excitation coil. In some embodiments, the excitation coil is provided in a patch or pad that is placed on the patient or on the operating table, although it can be positioned in any desired location within functional distance of the tags. In some embodiments, the remote activating device provides an AC magnetic field originating from one or more exciter antennas. In some embodiments, where the system is used to locate breast tumors, the patch encircles the treated breast or is placed otherwise near the breast. Similar approaches may be used for other targeted areas of a body. In some embodiments, a pad containing the excitation coil is placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions are detected by a detection component.

In some embodiments, the excitation coil or coils are contained in a belt that is placed around the subject or a portion of the subject. In some embodiments, the external excitation coil may further be used for other aspects of the patient care, such as for radiotherapy or to act as a ground current return pad used in electrosurgery. In some embodiments, the remote activating device emits light (e.g., laser light). In some embodiments, the remote activating device is configured for single use (e.g., is disposable).

In some embodiments, the remote activating device employs an unmodulated constant frequency activation (i.e., the activation signal has constant amplitude and frequency). In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency. In some embodiments, the remote activating device employs a pulsed frequency (i.e., the activation signal comprises brief excitation pulses at a periodic frequency, which may be comprised of two closely-related frequencies whose sum or difference is the response frequency of the tag). The pulsed activation produces a post-pulse sinusoidal decay signal. A tag alters the characteristic of the decaying signal, either in amplitude or time.

In some embodiments, the remote activating device comprises a hand-held component or a pad or pad-like component. In some embodiments, the hand-held component is lightweight to allow a surgeon to hold and manipulate the component over the course of a procedure (e.g., 5 kg or less, 4 kg or less, 3 kg or less, 2 kg or less, 1 kg or less, 0.5 kg or less, 0.25 kg or less, or any range therein between, e.g., 0.5 to 5 kg, 1 to 4 kg, etc.). In some embodiments, the hand-held component is shaped like a wand, having a proximal end that is held by the physician and a distal end that is pointed towards the treated subject or tissue harboring the tag. In some embodiments, the hand-held component is shaped like an otoscope, having a distal end that terminates at an angle (e.g., right angle) from the body of the component. In certain embodiments, the remote activating device comprises a pad or other flat component comprising at least one exciter antenna (e.g., solenoid coil). In some embodiments, the remote activating device comprises an exciter antenna that generates a magnetic field. In some embodiments, the remote activating device has only a single antenna (i.e., is monostatic). In some embodiments, the remote activating device has only two antennas (i.e., is bistatic). In particular embodiments, the remote activating device comprises multiple coils (e.g., solenoidal coils) arranged in sub-arrays that are substantially parallel to each other (e.g., as shown in FIG. 13). In certain embodiments, the coils (e.g., solenoidal coils) are sub-divided into two or more shorter coils sharing the same axis (e.g., as shown in FIG. 12).

In some embodiments, the magnetic field of the remote activating device is controlled by a processor running a computer program. In some embodiments, the remote activating device comprises a display or user interface that allows the user to control the remote activating device and/or monitor its functions while in use. In some embodiments, the remote activating device provides a visual, audio, numerical, symbol (e.g., arrows), textual, or other output that assists the user in locating the tag or identifying the distance to or direction of the tag from the remote activating device.

In some embodiments, the plurality of witness stations of the third component collectively provide several antennas at multiple defined locations relative to the tags and configured to receive a signal generated by the one or more tags upon being exposed to the magnetic field generated by the second component.

In some embodiments, each receiving antenna feeds a receiver channel, which is time-division multiplexed (TDM'd) to reduce the receiver complexity. Fixed witness stations of defined locations relative to the tag and each other (e.g., arrayed along the patient) contain one or more (e.g., one to three) witness antennas arranged in a locally orthogonal manner to sense various components of the AC magnetic field from the tag. In some embodiments, one or more or all of these witness antennas in the witness stations is also TDM'd into a receiver channel, reducing complexity, as well as cross-talk between antennas.

In some embodiments, witness antennas comprise or consist of a ferrite-loaded cylindrical coil antenna, tuned (e.g., with one or more capacitors in parallel) for resonance at the frequency of an exciter (e.g., tag or emitter), (e.g., 100-200 kHz). Typical dimensions of a witness antenna are 3-5 mm diameter and 8-12 mm length, although both smaller and larger dimensions may be employed.

In some embodiments, the witness stations are provided below the patient (e.g., in a pad, garment, or other device positioned below the patient). In some embodiments, the witness stations are integrated into a surgical table or imaging device in which a patient is placed during a medical procedure. In some embodiments, the witness stations are placed on the floor, wall, or ceiling of the operating room or in a medical transport vehicle. In some embodiments, the witness stations are integrated into or attached to a medical device used in the medical procedure.

In some embodiments, a fourth component provides a medical device location emitter to allow the system to determine the location, position, distance, or other characteristic of a medical device relative to the tag or tags. In some embodiments, the medical device location emitter or emitters are integrated into a medical device. In other embodiments, they are attachable to a medical device. In some such embodiments, the emitters are provided in a sleeve that slips over a portion of a medical device. The emitters may operate as and/or comprise the same materials as the tags, but are positioned on or near a medical device rather than within tissue. For example, in some embodiments, the emitters comprise coils that are excited with both carrier and/or sidebands, enabling the emitters to emit signals as though it were a tag.

In some embodiments, location of the emitters is accomplished geometrically by measuring the quasi-simultaneous power detected from the emitters at a plurality of witness stations (e.g., four or more stations), and using the power differences to perform vector math that determines the location of the emitter without ambiguity. This process is facilitated by a preliminary calibration using a known tag in a known location prior to the procedure.

Vectors describing the location of emitters are used to provide visualization guidance to the surgeon about the spatial relationship of a medical device (e.g., particularly its tip) to an implanted tag, or (e.g., with computational guidance) to a lesion boundary. Use of multiple emitters on a medical device provides vectors to determine the device's principal axis using the same vector math. Where a more complex medical device, such as a robotic surgical system (e.g., da Vinci surgical system) is employed, multiple emitters located on multiple different locations of the device are employed to provide location, orientation, and other position information of multiple components (e.g., arms) of the device. In some embodiments, the emitters are also used as detectors (e.g., provide witness stations on the medical device).

In some embodiments, a fifth component provides one or more computing systems comprising one or more computer processors and appropriate software to analyze, calculate, and display tag and emitter position information. In some embodiments, the display provides a graphical representation of the tag, patient, and/or medical device on a monitor. In other embodiments, the display provides directional information for moving or positioning the medical device. In some embodiments, the system automatically (e.g., robotically) controls the medical device or one or more functions thereof. In some embodiments, the display integrates tag and/or medical device information with previously obtained or concurrently obtained medical images of the patient or target tissue (e.g., CT, MRI, ultrasound, or other imaging modalities). For example, in some embodiments, an image indicating a tag or tags is fused with an image of the subject's tissue or body region obtained from an imaging device. In some embodiments, information is analyzed in real-time. In some embodiments, information is analyzed at one or more discrete time points.

In some embodiments, the fifth component provides command and control functions for a user of the system. In some embodiments, the fifth component has information stored thereon that helps guide the information displayed on the detection component. For example, the information may include data on the type of medical device the detection component is attached to, or what tip or cutting implement is being used with a particular medical device. In this regard, the precise location of the cutting tip of a medical device and its relation to the tag (e.g., distance to the tag) is communicated to the surgeon (e.g., for very precise instructions on cutting tissue). Such information is, for example in some embodiments, manually entered into a control unit or detection component by the user, or automatically found (e.g., by a barcode or other indicator) when a detection component is attached to a particular medical device.

The system finds use with a wide variety of medical devices and procedures. In some embodiments, the surgical device comprises an electrical surgical device that is turned on and off by a user, wherein a control unit that is part of the fifth component allows the remote activating device to generate the magnetic field when the electrical surgical device is off, and prevents the remote activating device from generating the magnetic field when the electrical surgical device is on (e.g., ensuring that the surgical device and detection system do not interfere with one another). In other embodiments, the surgical device comprises a power cord, wherein an AC current clamp is attached to the power cord, wherein the AC current clamp is electrically-linked or wirelessly linked to the control unit, wherein the AC current clamp senses when the electrical surgical device is on or off and reports this to the control unit (e.g., such that the control unit can ensure that the magnetic field from the surgical device and from the remote activating device are not active at the same time).

In certain embodiments, the surgical device comprises an electrocautery device, a laser cutting device, a plasma cutting device, or a metal cutting device (e.g., a surgical device manufactured by BOVIE MEDICAL). Additional examples of medical devices that find use in embodiments of the system are found, for example, in the following U.S. Pat. Nos. 9,144,453; 9,095,333; 9,060,765; 8,998,899; 8,979,834; 8,802,022; 8,795,272; 8,795,265; 8,728,076; 8,696,663; 8,647,342; 8,628,524; 8,409,190; 8,377,388; 8,226,640; 8,114,181; 8,100,897; 8,057,468; 8,012,154; 7,993,335; 7,871,423; 7,632,270; 6,361,532; all of which are herein incorporated by reference in their entireties, and particularly with respect to the hand-held medical devices disclosed therein.

In some embodiments, the medical device has thereon (e.g., provided as part of the fourth component) an indicator for directing the surgeon to the tag or tags. In some embodiments, the indicator provides: i) a spatial orientation indicator (e.g., visual, audible, etc.), and/or ii) a distance-to-tag indicator (e.g., visual, audible, etc.). In some embodiments, the indicator comprises a first display for presenting distance to tag information (e.g., visual, audible, lights, color, vibration, tactile, etc.), a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the indicator comprises a plurality of displays (e.g., visual, audible, sensory, etc.) that allow the correct pitch and yaw axes to be employed (to minimize non-target tissue damage), and/or further a display that provides distance to tag information. In certain embodiments, the medical device is moved around the patient's body prior to surgery to orient the emitters and the indicator component. In certain embodiments, a series of lights and/or sounds is provided on the indicator that guides the surgeon (e.g., the surgeon attempts to keep the lights in a center of an "X" series of lights, and/or to keep the volume of warning sounds off or as low as possible).

The tag is not limited to placement within a particular body region, body part, organ, or tissue. For example, in some embodiments, the tag is placed in the cephalic, cervical, thoracic, abdominal, pelvic, upper extremities, or lower extremities region of the body. In some embodiments, the tag is placed within an organ system, such as the skeletal system, muscular system, cardiovascular system, digestive system, endocrine system, integumentary system, urinary system, lymphatic system, immune system, respiratory system, nervous system or reproductive system. In some embodiments, the tag is placed within an organ. Such organs may include the heart, lungs, blood vessels, ligaments, tendons, salivary glands, esophagus, stomach, liver, gallbladder, pancreas, intestines, rectum, anus, hypothalamus, pituitary gland, pineal gland, thyroid, parathyroids, adrenal glands, skin, hair, fat, nails, kidneys, ureters, bladder, urethra, pharynx, larynx, bronchi, diaphragm, brain, spinal cord, peripheral nervous system, ovaries, fallopian tubes, uterus, vagina, mammary glands, testes, vas deferens, seminal vesicles, and prostate. In some embodiments, the tag is placed within tissues, such as connective, muscle, nervous, and epithelial tissues. Such tissues may include cardiac muscle tissue, skeletal muscle tissue, smooth muscle tissue, loose connective tissue, dense connective tissue, reticular connective tissue, adipose tissue, cartilage, bone, blood, fibrous connective tissue, elastic connective tissue, lymphoid connective tissue, areolar connective tissue, simple squamous epithelium, simple cuboidal epithelium, simple columnar epithelium, stratified epithelium, pseudostratified epithelium, and transitional epithelium.

In some embodiments, the tissue region where the tag is located comprises a lesion. In some embodiments, the lesion is a tumor or a tissue region identified as being at risk for forming a tumor. In some embodiments, the lesion is fibrotic tissue. In some embodiments, the lesion is an inflamed or infected region. In some embodiments, the tag is placed within a lumen to detect function or other process of the organ or provide localizing information. For example, the tag could be swallowed, or placed into a hollow organ via endoscopy. In some embodiments, the tissue region is healthy tissue.

In some embodiments, the tag is placed within a solid tumor. Examples of solid tumors into which the tag may be placed include carcinomas, lymphomas, and sarcomas, including, but not limited to, aberrant basal-cell carcinoma, acinar cell neoplasms, acinic cell carcinoma, adenocarcinoma, adenoid cystic carcinoma, adenoid/pseudoglandular squamous cell carcinoma, adnexal neoplasms, adrenocortical adenoma, adrenocortical carcinoma, apudoma, basal cell carcinoma, basaloid squamous cell carcinoma, carcinoid, cholangiocarcinoma, cicatricial basal-cell carcinoma, clear cell adenocarcinoma, clear cell squamous-cell carcinoma, combined small cell carcinoma, comedocarcinoma, complex epithelial carcinoma, cylindroma, cystadenocarcinoma, cystadenoma, cystic basal-cell carcinoma, cystic neoplasms, ductal carcinoma, endometrioid tumor, epithelial neoplasms, extramammary Paget's disease, familial adenomatous polyposis, fibroepithelioma of Pinkus, gastrinoma, glucagonoma, Grawitz tumor, hepatocellular adenoma, hepatocellular carcinoma, hidrocystoma, Hurthle cell, infiltrative basal-cell carcinoma, insulinoma, intraepidermal squamous cell carcinoma, invasive lobular carcinoma, inverted papilloma, keratoacanthoma, Klatskin tumor, Krukenberg tumor, large cell keratinizing squamous cell carcinoma, large cell nonkeratinizing squamous cell carcinoma, linitis plastica, liposarcoma, lobular carcinoma, lymphoepithelial carcinoma, mammary ductal carcinoma, medullary carcinoma, medullary carcinoma of the breast, medullary thyroid cancer, micronodular basal-cell carcinoma, morpheaform basal-cell carcinoma, morphoeic basal-cell carcinoma, mucinous carcinoma, mucinous cystadenocarcinoma, mucinous cystadenoma, mucoepidermoid carcinoma, multiple endocrine neoplasia, neuroendocrine tumor, nodular basal-cell carcinoma, oncocytoma, osteosarcoma, ovarian serous cystadenoma, Paget's disease of the breast, pancreatic ductal carcinoma, pancreatic serous cystadenoma, papillary carcinoma, papillary hidradenoma, papillary serous cystadenocarcinoma, papillary squamous cell carcinoma, pigmented basal-cell carcinoma, polypoid basal-cell carcinoma, pore-like basal-cell carcinoma, prolactinoma, pseudomyxoma peritonei, renal cell carcinoma, renal oncocytoma, rodent ulcer, serous carcinoma, serous cystadenocarcinoma, signet ring cell carcinoma, signet-ring-cell squamous-cell carcinoma, skin appendage neoplasms, small cell carcinoma, small cell keratinizing squamous cell carcinoma, somatostatinoma, spindle cell squamous cell carcinoma, squamous cell carcinoma, squamous cell lung carcinoma, squamous cell thyroid carcinoma, superficial basal-cell carcinoma, superficial multicentric basal-cell carcinoma, syringocystadenoma papilliferum, syringoma, thymoma, transitional cell carcinoma, verrucous carcinoma, verrucous squamous cell carcinoma, VIPoma, and Warthin's tumor.

In some embodiments, placing the tag comprises the steps of inserting an introduction device into the subject and introducing the tag through the introduction device into the subject. In some embodiments, the introduction device is a needle, cannula, or endoscope. In some embodiments, the tag is forced through the introduction device (e.g., via physical force, pressure, or any other suitable technique) and released into the subject at the distal end of the introduction device. After the tag is placed, the introduction device is withdrawn, leaving the tag at the desired location with the subject. In some embodiments, the introduction of the tag is guided by imaging technology.

In some embodiments, multiple tags are placed into the subject. The tags may be of identical type or may differ (e.g., differ in signal type). The tags may be placed in proximity to one another or at distant locations. Multiple tags are used, in some embodiments, to triangulate the location intended for medical intervention.

In some embodiments, the tags are further used as fiducials for radiotherapy (or other targeted therapy). The location of the tags is identified with an external reader and used to place, for example, laser light on the skin surface exactly where the chip is located. This eliminates the need to use X-ray, CT, or fluoroscopy to see the fiducials. This also decreases or eliminates the need to put skin markers (e.g., tattoos) on patients. This also helps in respiratory compensation as the fiducial moves up and down with a tumor in the lung or abdomen. Therefore, one can conduct real-time radiation only when the tumor is in the correct position and decrease damage to the background tissue (e.g., avoid burning a vertical stripe in the patient as the tumor moves up and down). The use as fiducials for director therapy (e.g., radiation therapy) also enhances triangulation as depth information (based on signal strength) assists in localization of the tumor to minimize collateral damage.

In some embodiments, provided herein are systems and methods employing one or more or all of: a) a tag (e.g., comprising an antenna; e.g., a coil antenna; e.g., a ferrite-core coil antenna; e.g., that resonates at 100-200 kHz; e.g., coupled to an integrated circuit); b) a remote activation device that generates a magnetic field within a region of the tag; and c) a plurality of witness stations, each of the witness stations comprising an antenna configured to detect information generated by said tag or a change in a magnetic field generated by the remote activation device caused by said tag. In some embodiments, the tag emits sidebands at defined frequencies upon activation by a magnetic field and the witness stations detect such sidebands. In some embodiments, the tag emits the sidebands at frequencies defined by a number programmed into a counter in the tag.

In some embodiments, the remote activating device comprises an excitation coil that is, for example, powered by a generator electrically connected to the remote activating device. In some embodiments, the remote activating device comprises a pad configured to be placed in proximity to (e.g., under, above, beside) a patient having the tag embedded in the patient. In some embodiments, the pad also contains the witness stations.

In some embodiments, the witness stations are tuned to a frequency of the sidebands. In some embodiments, each witness station comprises a plurality of antennas. In some embodiments, each witness station antenna feeds a receiver channel that is time-division multiplexed. In some embodiments, each antenna of a plurality of antennas within a witness station is arranged in an orthogonal manner to each other. In some embodiments, the witness station antennas comprise a ferrite-loaded cylindrical coil antenna tuned for resonance at a frequency of the signals to be detected (e.g., from a tag or emitter).

In some embodiments, the system further comprises one or more emitters configured for attachment to a medical device. Any type of attachment may be employed. The one or more emitters may be integrated with the device or may be added to the devices (e.g., via on a sheath that slides over a portion of the device). In some embodiments, the emitters are designed similarly to the tag. For example, in some embodiments, the one or more emitters comprise an antenna, wherein the emitters emit sidebands at defined frequencies upon activation by a magnetic field. In some embodiments, the one or more emitters comprise at least two emitters positioned to permit the witness stations to detect orientation of said medical device relative to the tag.

In some embodiments, the system further comprises a computer system that receives information from the plurality of witness stations and generates information about the position of the tag and/or the medical device. In some embodiments, the system further comprises a display that displays the generated information to a user. In some embodiments, the display is on a monitor or on a medical device.

In some embodiments, provided herein are systems and methods comprising: a) a tag; b) an emitter attached to a medical device; c) a remote activation device that generates a magnetic field within a region of the tag and the emitter; and d) a plurality of witness stations, each said witness station comprising an antenna configured to detect information: i) emitted from the tag or changes in a magnetic field generated by the remote activating device in response to the tag; and/or ii) emitted from the emitter or changes in a magnetic field generated by the remote activating device in response to the emitter.

Also provided herein are uses of any of the above systems (e.g., for detecting a position of a tag in an object; for detecting a position of a tag relative to a medical device; etc.). Further provided herein are methods of identifying a position of a tag, comprising: a) providing any of the systems described herein; b) placing the tag in an object; c) generating a magnetic field with the activating device; and d) identifying a position of said tag in said object by collecting information emitted from the tag with the witness stations. In some embodiments, the position or comprises relative location or distance of the tag to a medical device.

Also provided herein are systems, devices, assemblies, and methods for localization of a tag in a tissue of a patient. For example, provided herein are systems, devices, and methods employing a detection component that is attached to or integrated with a surgical device, where the detection component detects a signal from a tag in a patient, where the tag is activated by remote introduction of a magnetic field. In certain embodiments, the detection component comprises three or more sense coils to triangulate a tag location and the distance of the tag from the detection component.

In some embodiments, provided herein are methods for localizing a tissue region of a patient, comprising: a) placing a remote activating device and a patient in proximity to each other, wherein the remote activating device is able to generate a magnetic field, and wherein a tag is located in a tissue of the patient; and b) localizing the tag in the patient by generating a magnetic field with the remote activating device and detecting a signal from the tag using a detector component, wherein the detector component comprises at least one sense coil and is attached to, or integrated with, a surgical device, and wherein the detector component and remote activating device are separate (e.g., not attached to, or part of, each other).

In certain embodiments, the at least one sense coil comprises three sense coils that are separated from each other by at least 10 mm (e.g., at least 10 . . . 15 . . . 20 . . . 25 . . . 30 . . . 40 . . . 50 . . . 60 . . . 70 . . . 100 . . . 125 . . . 150 . . . 175 . . . or 200 mm). In other embodiments, the at least one sense coil comprises three sense coils arranged in a triangle. In particular embodiments, the triangle is an equilateral triangle or approximately an equilateral triangle.

In particular embodiments, the detector component comprises a housing with a device-securing component (e.g., an opening in the housing; a snap; tongue and groove; slot; magnetic attachment; etc.). In some embodiments, the surgical device is in inserted through the device-securing opening such that the housing surrounds a portion of the surgical device (and such that said surgical device is secured to said detection component).

In certain embodiments, the remote activating device, the detector component, and the surgical device are electrically-linked and/or wirelessly linked to a control unit, wherein the control unit comprises a processor and control software. In further embodiments, the detection component comprises a display (e.g., visual, audible, etc.), and wherein the control unit processes signals from the detection component and provides data that is displayable on the display. In particular embodiments, the surgical device comprises an electrical surgical device that is turned on and off by a user, wherein the control unit allows the remote activating device to generate the magnetic field when the electrical surgical device is off, and prevents the remote activating device from generating the magnetic field when the electrical surgical device is on (e.g., ensuring that the surgical device and detection system do not interfere with one another). In other embodiments, the surgical device comprises a power cord, wherein an AC current clamp is attached to the power cord, wherein the AC current clamp is electrically-linked or wirelessly linked to the control unit, wherein the AC current clamp senses when the electrical surgical device is on or off and reports this to the control unit (e.g., such that the control unit can ensure that the magnetic field from the surgical device and from the remote activating device are not active at the same time).

In certain embodiments, the control, unit and/or detection component, has information stored thereon that helps guide the information displayed on the detection component. For example, the information may include data on the type of medical device the detection component is attached to, or what tip or cutting implement is being used with a particular medical device. In this regard, the precise location of the cutting tip of a medical device and it's relation to the tag (e.g., distance to the tag) can be communicated to the surgeon (e.g., for very precise instructions on cutting tissue). Such information can, for example, be manually entered into the control unit or detection component by the user, or automatically found (e.g., by a barcode or other indicator) when a detection component is attached to a particular medical device.

In some embodiments, the remote activating device comprises one or more excitation coils. In further embodiments, the remote activating device comprises a pad, and wherein the pad is placed under the patient or under a bed the patient is on. In other embodiments, the signal is an irregularity (e.g., interruption or perturbation) in the magnetic field caused by the tag. In other embodiments, the tag comprises a metal particle (e.g., a ferrite particle).

In other embodiments, the detector component comprises an electronics component, wherein the electronics component comprises a signal processor. In certain embodiments, the detector component comprises an electronics component, wherein the electronics component comprises: i) a spatial orientation indicator (e.g., visual, audible, etc.), and/or ii) a distance-to-tag indicator (e.g., visual, audible, etc.). In further embodiments, the tissue region is selected from the group consisting of: a lesion, a tumor, a breast tumor, a blood vessel, a lymph node, and sentinel node.

In certain embodiments, the detector component comprises a first display for presenting distance to tag information (e.g., visual, audible, lights, color, vibration, tactile, etc.), a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the detector components comprises a plurality of displays (e.g., visual, audible, sensory, etc.) that allow the correct pitch and yaw axes to be employed (to minimize non-target tissue damage), and/or further a display that provides distance to tag information. In certain embodiments, the detector component is moved around the patient's body prior to surgery to orient the detector component. In certain embodiments, a series of lights and/or sounds are provided on the detector component that guide the surgeon (e.g., the surgeon attempts to keep the lights in a center of an "X" series of lights, and/or to keep the volume of warning sounds off or as low as possible). For example, the detector component may have an array or geometric shape of lights of different colors that can light up informing the user (e.g., doctor) with regard to location of a tag and/or position of the detector component (and corresponding surgical instrument), such that the user does not have to look away from the surgical field or procedure field.

In some embodiments, the signal comprises: i) a signal detectable by sensory perception; ii) an interruption or perturbation in the magnetic field; or iii) light. In further embodiments, the tag comprises: a radio-frequency identification (RFID) chip; ii) a resonant or self-resonant object; or iii) a metal particle. In other embodiments, the tag has a length, width, and depth, wherein the length is less than 10 mm, the width is less than 4 mm, and the depth is less than 4 mm. In other embodiments, the localizing comprises detecting a change based on intensity, frequency, color, or sound of the signal. In certain embodiments, the tag in the tissue of the patient is detected at a depth of at least 1 mm . . . 10 mm . . . 45 mm . . . 95 mm . . . 125 mm . . . 174 mm . . . or 200 mm.

In certain embodiments, the methods further comprise the step of surgically removing a tumor from the patient. In additional embodiments, the methods further comprise the step of administering radiation therapy to the patient using the tag as a fiducial. In other embodiments, the patient comprises a plurality of tags, and wherein the methods further comprise the step of determining locations of the plurality of tags to localize the tissue region in three dimensional space.

In some embodiments, the tip of the localizing device (e.g., such as a surgical instrument or an electrocautery system) is placed in a specific location (e.g., a jig containing a tag at a known distance and orientation from the tip) for calibration. This may require, for example, entering data into the system to describe the length or shape of the instrument.

In some embodiments, provided herein are systems comprising: a) a detector component comprising a housing and at least one sense coil inside the housing, wherein the detector component detects a signal from a tag inside a patient; and b) a second component selected from the group consisting of: i) a surgical instrument, ii) a remote activating device which generates a magnetic field, iii) a tag that is insertable at a location in a tissue of a patient, and iv) a control unit comprising a processor and a control software, wherein the control unit, when electrically or wirelessly linked to the detector component, provides data to the detector component.

In certain embodiments, the at least one sense coil comprises three sense coils that are separated from each other by at least 10 mm (e.g., at least 10 . . . 25 . . . 45 . . . 55 . . . 75 . . . 137 . . . 168 . . . or 200 mm). In other embodiments, the at least one sense coil comprises at least three sense coils arranged in a triangle. In particular embodiments, the triangle is an equilateral triangle or approximately an equilateral triangle. In certain embodiments, the housing has a device-securing component (e.g., opening in housing; slot; snap; etc.). In other embodiments, the second component comprises the surgical device, and wherein the surgical device is in inserted through the device-securing opening such that the housing surrounds a portion of the surgical device and the surgical device is secured to the housing. In certain embodiments, the surgical instrument comprises a hand-held surgical instrument.

In particular embodiments, the tag generates the signal when exposed to the magnetic field. In further embodiments, the signal is an irregularity in the magnetic field. In other embodiments, the detection component further comprises a display (e.g., visual, audible, tactile, etc.), and wherein the control unit processes signals from the detection component and provides the data that is displayable on the visual display. In other embodiments, the data comprises distance to tag data and/or orientation data. In some embodiments, wherein the control unit, when electrically or wirelessly linked to the detector component and the remote activating component, causes the remote activating device to generate the magnetic field when the electrical surgical device is off, and prevents the remote activating device from generating the magnetic field when the electrical surgical device is on. In other embodiments, the surgical device comprises a power cord, wherein an AC current clamp is attached to the power cord.

In some embodiments, the surgical device comprises an electrocautery device, a laser cutting device, a plasma cutting device, or a metal cutting device. In other embodiments, the remote activating device comprises an excitation coil. In some embodiments, the remote activating device comprises a pad or other generally flat component.

In certain embodiments, the tag comprises a metal particle (e.g., ferrite particle). In some embodiments, the detector component comprises an electronics component, wherein the electronics component comprises a signal processor. In some embodiments, the detector component comprises an electronics component, wherein the electronics component comprises: i) a visual spatial orientation indicator, and/or ii) a distance-to-tag indicator. In certain embodiments, the tag has a length, width, and depth, wherein the length is less than 10 mm, the width is less than 4 mm, and the depth is less than 4 mm.

In some embodiments, provided herein are detector components comprising: i) a housing having a device-securing component (e.g., opening in housing; snap; slot; etc.); and ii) at least one sense coil inside the housing, wherein the detector component detects a signal from a tag inside a patient. In further embodiments, the at least one sense coil comprises three sense coils that are separated from each other by at least 10 mm (e.g., 10 mm 50 . . . 200 mm). In certain embodiments, the at least one sense coil comprises at least three sense coils (e.g., arranged in a triangle, or otherwise able to triangulate the position and distance of tag). In other embodiments, the triangle is an equilateral triangle or approximately an equilateral triangle. In further embodiments, the detector component further comprises an electronics component, wherein the electronics component comprises a signal processor. In other embodiments, the detector component further comprises an electronics component, wherein the electronics component comprises: i) a spatial orientation indicator, and/or ii) a distance-to-tag indicator.

In certain embodiments, provided herein are detector components comprising: i) a housing; and ii) at least three sense coils inside the housing (e.g., arranged in a triangle or otherwise able to triangulate the position and distance of the tag) wherein the detector component is able to detect a signal from a tag inside a patient. In some embodiments, the three sense coils that are separated from each other by at least 10 mm (e.g., 10 mm . . . 100 mm . . . 200 mm). In other embodiments, the triangle is an equilateral triangle or approximately an equilateral triangle. In additional embodiments, the detector component further comprises an electronics component, wherein the electronics component comprises a signal processor. In certain embodiments, the detector component further comprises an electronics component, wherein the electronics component comprises: i) a spatial orientation indicator, and/or ii) a distance-to-tag indicator. In some embodiments, the housing has a device-securing opening therein.

In particular embodiments, provided herein are devices comprising: a) a hand-held surgical instrument, and b) a detector component attached to, or integrated with, the hand-held surgical instrument, wherein the detector component comprises a housing and at least one sense coil inside the housing, wherein the detector component is able to detect an irregularity in a magnetic field.

In some embodiments, the at least one sense coil comprises three sense coils that are separated from each other by at least 10 mm . . . 30 mm . . . 50 mm . . . or 200 mm. In other embodiments, the at least one sense coil comprises three sense coils arranged in a triangle or other arrangement able to triangulate the location of a tag in a patient. In certain embodiments, the triangle is an equilateral triangle or approximately an equilateral triangle. In other embodiments, the detector component comprises a housing with a device-securing component (e.g., opening therein, snap, slot, or other connector) and wherein the surgical device is attached to the detection component via the device-securing component (e.g., surgical device is in inserted through the opening such that the housing surrounds a portion of the surgical device). In other embodiments, the hand-held surgical instrument comprises an electrocautery device, a laser cutting device, a plasma cutting device, or a metal cutting device. In additional embodiments, the hand-held surgical instrument comprises a power cord, and wherein an AC current clamp is attached to the power cord. In other embodiments, the detector component comprises an electronics component, wherein the electronics component comprises a signal processor. In further embodiments, the detector component comprises an electronics component, wherein the electronics component comprises: i) a spatial orientation indicator (e.g., display), and/or ii) a distance-to-tag indicator.

In some embodiments, the tag comprises a self-resonant object (e.g., a small ferrite core with a wound inductor). The wound inductor possesses inter-winding capacitance that in combination with the inductance produces a high frequency resonant circuit. In some embodiments, the tag comprises a resonant object (e.g., self-resonant object is equipped with a chip capacitor to produce resonance at a prescribed frequency). In some embodiments, the tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, a magnetic field and/or other sensing modality is provided by a remote activating device. In some embodiments, the remote activating device causes the activation event when in proximity (e.g., within a meter, . . . 0.5 meters, . . . 0.3 meters, . . . 0.2 meters, . . . 0.1 meters, . . . 0.05 meters, . . . , etc.) to the tag. In some embodiments, the intensity of the signal increases with closer proximity of the activating device and the tag. In some embodiments, the tag does not comprise any energy storage devices (e.g., battery, capacitor, etc.).

In some embodiments, the remote activating device employs an unmodulated constant frequency activation (i.e., the activation signal has constant amplitude and frequency). In some embodiments, the tag produces an irregularity in the activation field. The sensing method detects a shift in either amplitude or frequency induced by the tag's presence.

In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency.

In some embodiments, the detection component comprises a series of lights (LEDs) (e.g., 5 lights) which are lit to indicate proximity, distance, or direction to the tag. In some embodiments, the user has control over the strength of the magnetic field produced by the remote activating device. In some embodiments, internal algorithms embodied in the software control the magnetic field. In some embodiments, the user may select one or more algorithms from a menu. In some embodiments, algorithms reduce or increase the sensitivity of the remote activating device based on its distance from the tag. In certain embodiments, the display on the detection component displays numerals (e.g., numbers on an LCD screen for reporting distance).

In some embodiments, an image from an imaging component is associated with data collected by the detection component. In some such embodiments, a user display provides an image of the tissue from the subject (e.g., obtained from MRI, CT, ultrasound, or other imaging modality) and overlays information about the location of the tag, the detection component, and/or a surgical tool used by the surgeon.

In some embodiments, the remote activating device comprises an excitation coil. In some embodiments, the excitation coil is provided in a patch or pad that is placed on the patient or on the operating table. In some embodiments, where the system is used to locate breast tumors, the patch encircles the treated breast or is placed otherwise near the breast. In some embodiments, a pad containing the excitation coil is placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions (in some embodiments at a higher harmonic of the excitation or in some temporal or spectral combination unique to the tag) are detected by the detection component.

In some embodiments, the detection component is attached to or integrated with a surgical device, such as an electrosurgical device (e.g., electrocautery device such as a BOVIE device), cutting device, ablation device, or the like. A single housing may contain all components of the detection component and the surgical device. Alternatively, a bracket or other component is used to connect a component of a detection component to a surgical device. In some embodiments, a holder is used to mount both the electrosurgical device and the detection component together. In some embodiments, the detection component or a component thereof is attached to or integrated into another type of medical device that is used in the desired surgical procedure (e.g., clamps, endoscopes, bronchoscopes, extended bronchoscopes, dissection tools, lasers, laparoscopes, thoracoscopes, etc.).

Further provided herein are systems comprising the above tags, remote activating devices, and detection component. For example, systems may comprise the tag and detection component. Systems may further comprise other hardware (e.g., RFID reader), software, instructions, medical devices (e.g., cutting tools, imaging devices, tissue ablation devices, syringes, introduction needles/cannulas/endoscopes, sterilization components, etc.), pharmaceuticals, or other components useful, necessary, or sufficient for conducting a procedure with the tag. In some embodiments, the system comprises a computer that provides command and control functions for the tag and/or detection component. In some embodiments, the software collects and analyzes procedure data, information from an RFID chip, or other information generated during a procedure using the tag. In some embodiments, a computer comprises a display for displaying information to the treating physician, radiologist, patient, or other personnel involved in a procedure.

In certain embodiments, a fiduciary or localizing system is placed during an endoscopic procedure. For example, during colonoscopy, gastroscopy, duodenoscopy, cystoscopy, etc., a fiducial could be attached to a polyp or other mass. This fiducial is then localized during a subsequent procedure such as, for example, a laparoscopic colon resection or other procedure.

In some embodiments, the tag comprises a fixing component on the outer surface (e.g., of the housing, if present) to anchor the tag in the desired location. In some embodiments, the fixing component is a hook, barb, or other physical extension. In some embodiments, the fixing component is deployable upon placement. In some embodiments, the fixing component is a textured surface. In some embodiments, the fixing component is an adhesive.

It will be appreciated that the systems and methods described herein may be applied to other uses, including non-medical uses. The technology finds use in any situation where localization of a tag is desired, including, but not limited to, surgical procedures, diagnostic procedures, veterinary procedures, food analysis, industrial applications, and environmental applications.

DEFINITIONS

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape. In certain embodiments, the computer memory and computer processor are part of a non-transitory computer (e.g., in the control unit). In certain embodiments, non-transitory computer readable media is employed, where non-transitory computer-readable media comprises all computer-readable media with the sole exception being a transitory, propagating signal.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. For example, a conference bridge that is connected to a processor through a cable or wire, such that information can pass between the conference bridge and the processor, are in electronic communication with one another. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject/patient suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiment, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

DETAILED DESCRIPTION

Figure 1:
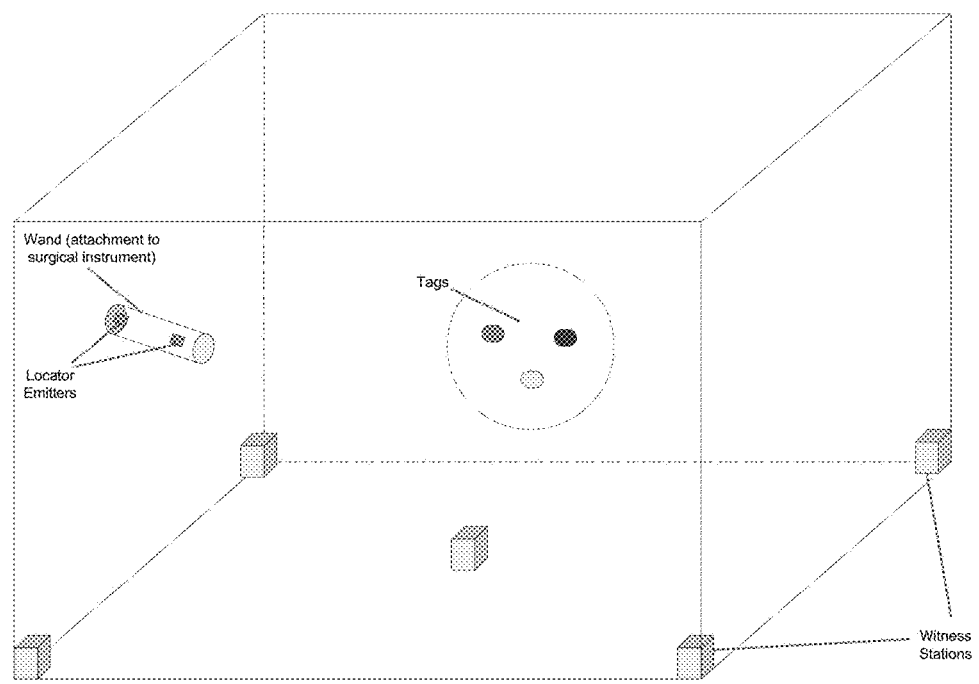
FIG. 1 shows an exemplary 3-dimensional positioning of tags, witness stations, and locator emitters on a wand configured to fit over a medical device.

Provided herein are systems, devices, assemblies, and methods for localization of one or more tags in a patient (e.g., in a tissue of a patient). For example, provided herein are systems, devices, and methods employing an implantable tag that emits sidebands at defined frequencies upon activation by a magnetic field generated by a remote activating device, and a plurality of witness stations configured to detect such sidebands. Also provided herein are herein are systems, devices, and methods employing a detection component that is attached to or integrated with a surgical device.

Also provided herein, for example, are systems, devices, and methods employing one or more or all of: a) one or more tags placed into an object, such as a patient; b) a remote activating device that generates an electromagnetic field within a region of the one or more tags; c) a plurality of witness stations that receive information from the one or more tags that have been exposed to the electromagnetic field; d) one or more emitters positioned on a medical device that are exposed to the electromagnetic field and that emit information received by the witness stations; and e) a computer system for analyzing information received by the witness station and generating and displaying information about the positions of the medical device and/or tag or tags (e.g., relative location, relative distance, orientation, etc.).

The systems and methods may be used in any context where the position of a tag is desired and/or where the relative position of another device (e.g., a medical device) is relative to a tag or tags. While the specification focuses on medical uses in human tissues, it should be understood that the systems and methods find broader use, including non-human uses (e.g., use with non-human animals such as livestock, companion animals, wild animals, or any veterinary settings). For example, the system may be used in environmental settings, agricultural settings, industrial settings, or the like.

In some preferred embodiments, the tag comprises a coil antenna. In some embodiments, the coil antenna is a ferrite-core coil antenna. In some embodiments, the coil antenna resonates at 100-200 kHz. In some embodiments, the coil antenna is coupled to an integrated circuit (IC). In some embodiments, the IC is powered by an AC magnetic field at resonance (e.g., provided by an activating device). In some embodiments, the coil antenna is provided in an enclosure (e.g., a glass or plastic enclosure). In some embodiments, the tag (with enclosure, if present) has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). In some embodiments, the tag, with enclosure, is shaped as an approximately 2×4 mm cylinder or smaller.

In some embodiments, the tag amplitude-modulates (AM's) the continuous wave (CW) carrier power from the magnetic field from the activating device, thus emitting sidebands at frequencies defined by a number programmed into the tag's counter. These sidebands, as well as the much stronger CW carrier if desired, are detected for the purpose of analyzing the position of the tag. The use of side bands permits a corresponding detector or detectors (e.g., witness stations) to detect the specific signal from the tag (e.g., using a lock-in amplifier tuned to the side band), without detecting background noise. This allows for precise, real-time detection and analysis of one or more tags, including analysis of relative position and distance from another object (e.g., a medical device).

In some embodiments, the remote activating device comprises a lock-in amplifier or device similar to a lock-in amplifier. In some embodiments, the lock-in type amplifier is configured for narrow-band detection to provide an omnidirectional detection system for determining location of the tag. In some embodiments, a modulating signal is employed and a higher harmonic caused by nonlinearity by the tag is detected. For example, a 40 kHz signal may be provided and the system looks for a 2nd harmonic of 80 kHz generated when the tag is present. The nonlinearity may be a semiconductor diode junction excited by current flowing through a coil of the tag.

In some embodiments, as an alternative to use of a lock-in type amplifier, cavity ringdown is employed. Temporal pulses are emitted and the detector looks for resonator decay over time. Not only is the phase and frequency of the ringdown signal specific to the particular tuning of the tag, but also the exponential decay (to a given threshold) of the ringdown signal's envelope is a relative indicator of the tag's distance from the excitation source.

Any number of other tag designs may be employed. In some embodiments, the tag comprises or consists of a ferrous pellet or particle. When the ferrous object is introduced within a magnetic field, the object creates an irregularity in the alternating magnetic field which is detectable by sense coils contained within witness stations, producing a phase and amplitude shift from null. The null is restored when the ferrous object is physically equidistant to two sense coils.

In some embodiments, the tag comprises a self-resonant object (e.g., a small ferrite core with a wound inductor). The wound inductor possesses inter-winding capacitance that in combination with the inductance produces a high frequency resonant circuit. Detection occurs, for example, using the approach described above for the ferrous pellet or, for example, using a Grid Dip Oscillator (GDO). The GDO has a resonant circuit that radiates an electromagnetic field. When proximal to the self-resonant object of the same frequency, power transfer from the GDO to the self-resonant object induces a detectable change in the GDO power. In some embodiments, the tag comprises a resonant object (e.g., self-resonant object is equipped with a chip capacitor to produce resonance at a prescribed frequency). In some embodiments, the tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the activating device (or other device) and then acts as a passive transponder to emit microwaves or UHF radio waves. In some embodiments, a reader (which can be part of the activation device or another device) sends a signal to the RFID chip and reads its response. In some embodiments, the RFID chip is read-only. In other embodiments, it is read/write.

The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (e.g., after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, the tag is configured for single-use. In some such embodiments, a tag can be disabled or deactivated (e.g., like an EAS tag). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the localization tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the device in place, avoiding migration in tissue. These struts may deploy upon placement in tissue. In some embodiments the fastener may be a biocompatible material that bonds with surrounding tissue. In some embodiments, the tag comprises an anti-migration surface. In some embodiments, the anti-migration surface is textured to reduce movement of the tag when in contact with tissue or a target location. The anti-migration feature may be made of any desired material, including, but not limited to titanium, nitinol, polyethylene, terepthalate, nylon, polyethylene, polytetrafluoroethylene, polypropylene, polyurethane, polyamide, silicone, and combinations thereof.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.). In some embodiments, the tag does not comprise any power source. For example, in some embodiments, the signal is generated from the signal source in response to a magnetic field as the activation event (i.e., electromagnetic induction).

Figure 4:
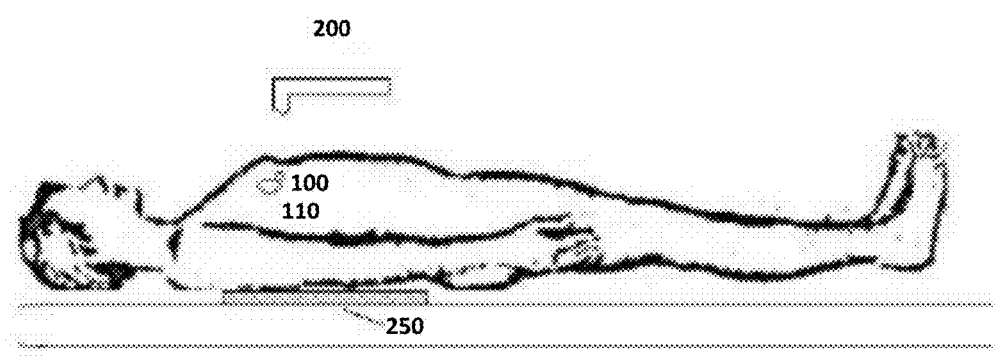
FIG. 4 shows an exemplary positioning of tags, a pad comprising a remote activating device and/or witness stations, and a medical device.
Figure 5A:
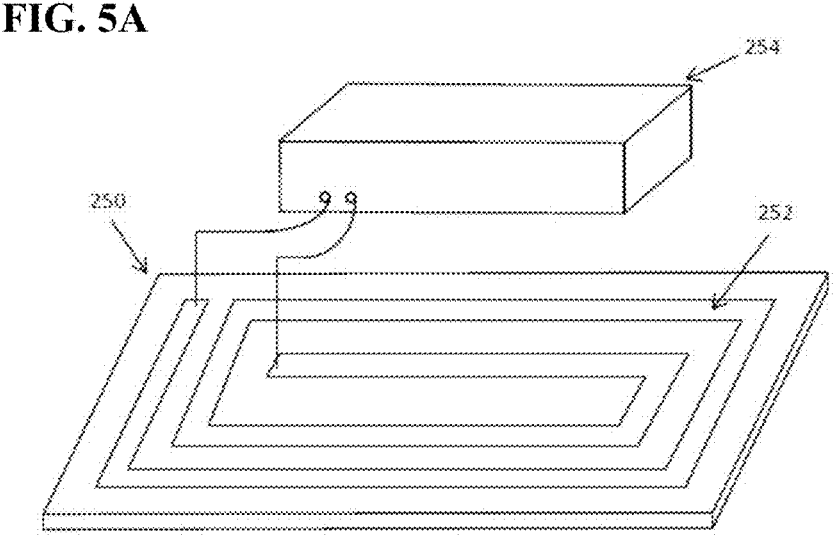
FIG. 5A shows an exemplary power supply connected to coils positioned within a remote activating device.

In some embodiments, the remote activating device comprises one or more excitation coils contained in a flat pad. In some embodiments, the pad is sized and shaped to fit beneath a patient during a medical procedure. The pad may be integrated or placed on a surgical table or imaging system, may be integrated into the patient's clothing, or otherwise placed in the surgical field. FIG. 5A provides exemplary remote activating device 250 containing an excitation coil 252 and connected to a generator 254 by wires. FIG. 4 shows an exemplary placement of the remote activating device 250 between a surgical table and a subject, the subject having a tissue mass (e.g., tumor) 110 and a tag 100 inserted near the tissue mass 110. A medical device 200 is positioned above the patient. The tag 100 and the medical device 200 are within range of a magnetic field that is generated by the remote activating device 250. In some embodiments, the excitation source of the activation device is a synthesized and stabilized frequency source (e.g., oscillator) whose output is gain-controlled (e.g., via an intermediate amplifier) and provided to a power amplifier to maintain adequate power levels for driving the implanted tag or emitter on a medical device.

Figure 6:
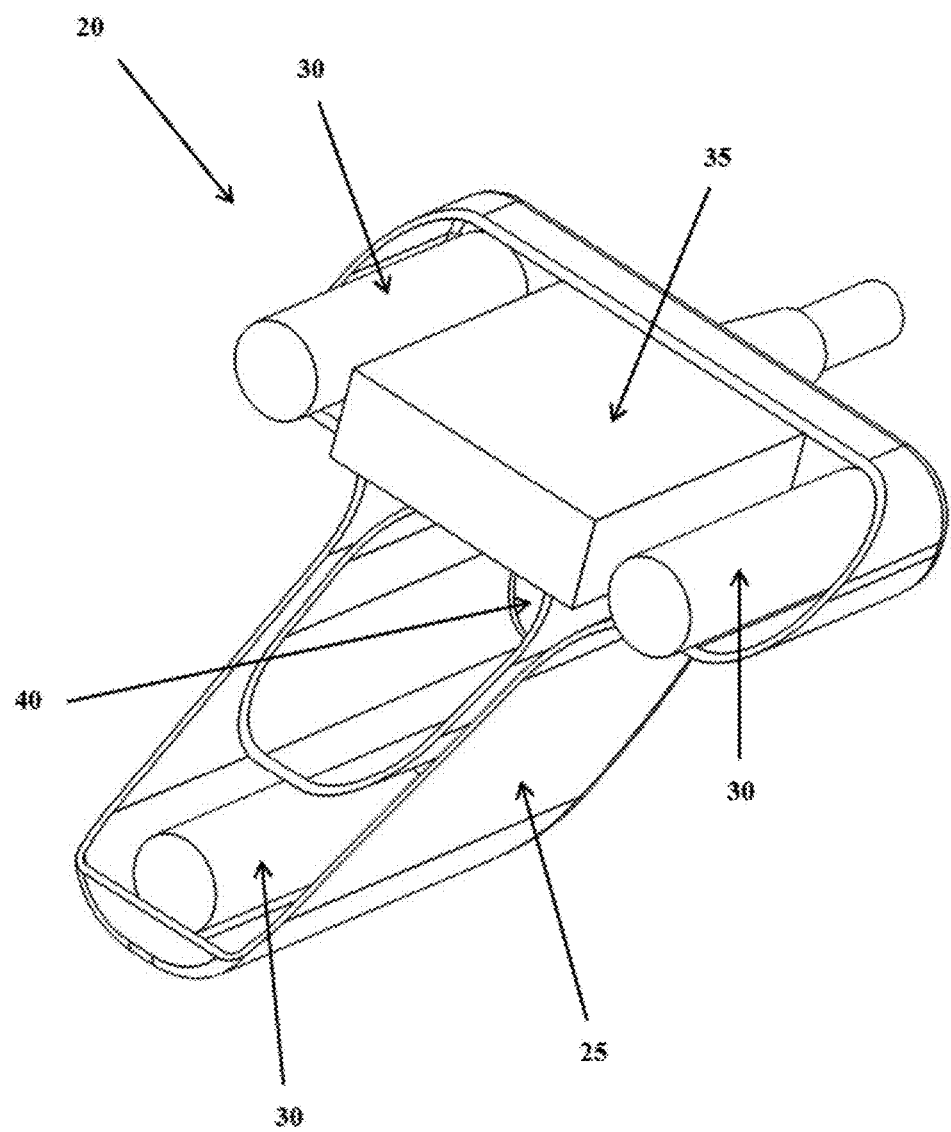
FIG. 6 shows an exemplary detection component (20) having a detection component housing (25) which contains three sense coils (30) and an electronics component (35). The housing (25) also has a device-securing opening (40) therein.

In some embodiments, the witness stations are also included in the same device (e.g., pad) as the remote activating device. In other embodiments, they provided in a different device. In some embodiments, witness stations are provided on or associated with a medical device. For example, FIG. 6 shows a component 20 configured to fit around a medical device that comprises a housing 25 that contains three witness stations 30 that are arrange in a triangle configuration and an electronics component 35 for receiving and processing signals received by the witness stations. The housing 25 has a device-securing opening 40 therein, that allows a medical device to be inserted and secured in place.

In some embodiments, each witness antenna comprises or consists of a ferrite-loaded cylindrical coil antenna, tuned (e.g., with one or more capacitors in parallel) for resonance at the frequency of an exciter (e.g., tag or emitter) (e.g., typically 100-200 kHz). Typical dimensions of a witness antenna are 3-5 mm diameter and 8-12 mm length, although both smaller and larger antenna may be employed. In some embodiments, witness station antenna has a ferrite core size of 0.25×1 inch and contains 75-80 turns of a 10/46 (10 strands of #46) Litz wire which provides 0.157 mH (Q=53) (75 Turns).

Figure 3:
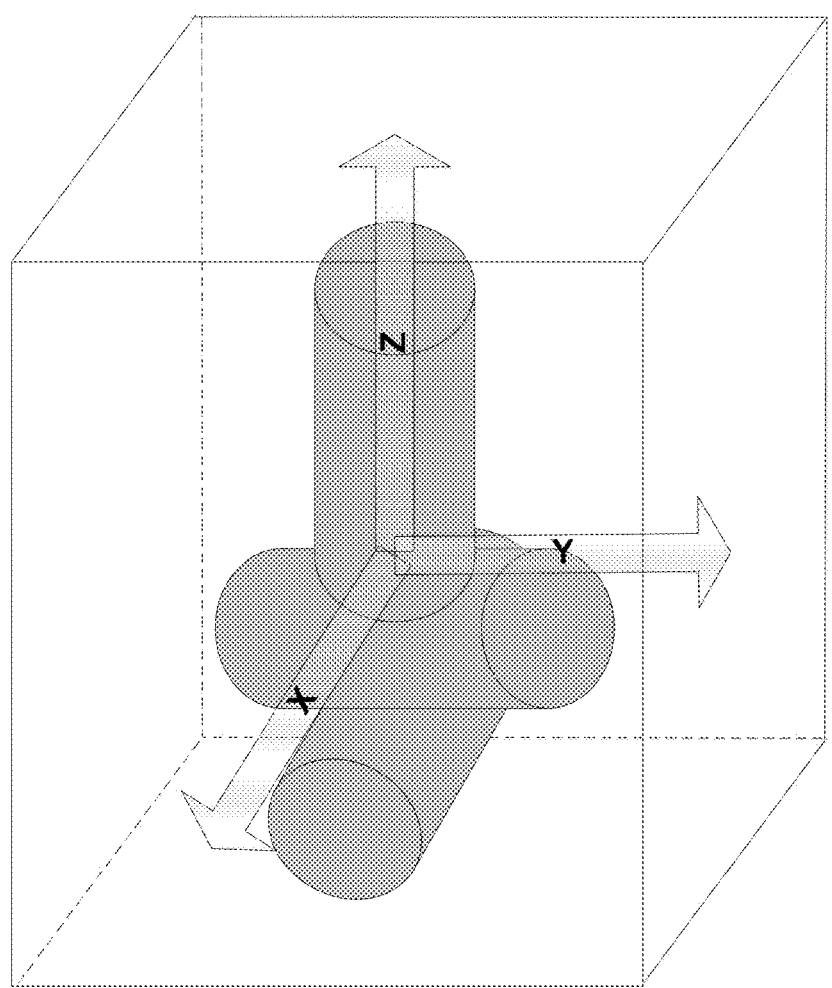
FIG. 3 shows an exemplary witness station configuration having three orthogonal coils arranged to minimize cross-talk.

In some embodiments, each witness station contains 1-3 witness antennas oriented orthogonally to each other and further arranged to have minimum cross-talk (i.e., interference with one another). FIG. 3 shows an exemplary configuration with three antennas, one oriented in the x plane, one in the y plane, and one in the z plane.

Figure 2:
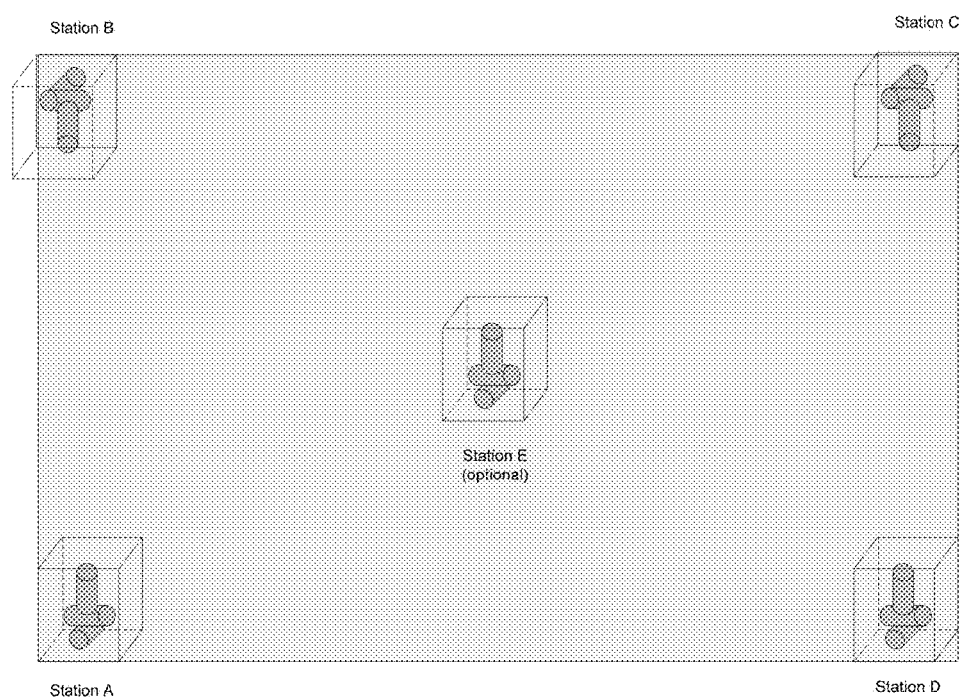
FIG. 2 shows an exemplary pad configuration with multiple witness stations.

FIG. 2 shows an exemplary arrangement of witness stations within a flat pad with four witness stations positioned at each of the four corners (labeled Station A, Station B, Station C, and Station D) and a fifth optional station (Station E) positioned in the center. Any number of stations may be employed (e.g., 1, 2, 3, 4, 5, 6, 7, 8, 9, 10, 11, 12, etc.) in any desired position and orientation.

FIG. 1 shows an exemplary configuration of a witness station configuration as shown in FIG. 2 in three-dimensional space relative to three tags located in an object above the witness station and relative to a wand (e.g., attached to a surgical instrument) having two locator emitters.

The component housing the witness stations further comprises one or more receiver channels for collecting information obtained by the antennas of the witness stations. In some embodiments, the receiver comprises or consists of one or more channels, each channel fed by one or more (via a multiplexing switch) witness antennas.

In some embodiments, location of an implanted tag or an emitter on a medical device is accomplished geometrically by measuring the quasi-simultaneous power detected from these tags at multiple (e.g., four or more) witness stations, and using the power differences to perform vector math that determines the location of the tag without ambiguity. In some embodiments, this process is facilitated by a preliminary calibration using a known tag in a known location prior to the procedure.

In some embodiments, vectors describing the location of implanted tags or medical device emitters are used to provide visualization guidance to the surgeon about the spatial relationship of the medical device (particularly its tip) to the implanted tag, or (with computational guidance) to a lesion boundary. Multiple emitters on the medical device further provide vectors to determine the medical device's principal axis using the same vector math.

In some embodiments, the component comprising the witness stations comprises an analog front-end. For example, the analog input to the receiver may comprise or consists of a current-to-voltage (transimpedance instrumentation) preamplifier (http://www followed by analog.com/en/products/amplifiers/instrumentation-amplifiers/ad8421.html#product-overview) whose output drives a synchronous detector (http://www.Followed by analog.com/en/products/rf-microwave/iq-modulators-demodulators/iq-demodulators/ad630.html#product-overview) that takes the unknown signal from the witness antennas and compares it to the known CW exciter signal, effectively filtering out the strong exciter signal and providing the amplitude modulation frequency of the tag as its output. This function is similar to that of a lock-in amplifier, where the (unmodulated) frequency reference is used to place a narrow-band notch filter onto the reference, recovering a much smaller modulation in the presence of noise.

In some embodiments, subsequent stages in the analog front-end provide additional bandpass and low-pass filtering and gain. For example, in some embodiments, the output of these stages is provided to a precision rectifier to directly determine a DC voltage proportional to the received signal strength from the instant antenna, or the unrectified signal is digitized using conventional D/A techniques.

In some embodiments, a digital back-end of the receiver accepts as input either a digital version of the DC voltage level or first performs a digital demodulation of the AC signal. Either approach results in a numerical indication of the signal strength due to the instant antenna. This signal varies with distance d between the instant witness antenna and the tag according to an inverse integer power relationship, e.g. $1/d^6$. Detailed considerations of the variation of signal strength with distance are found in http://robotics. followed by eecs.berkeley.edu/~pister/290Q/Papers/Antennas%20propagation%20interference/near%20field%20path%20loss.pdf, which is a paper entitled "A Near Field Propagation Law & A Novel Fundamental Limit to Antenna Gain Versus Size," submitted to IEEE APS Conference July 2005," author is Dr. Hans Schantz, and which is herein incorporated by reference as if fully set forth herein.

Consulting the above reference and inverting the experimentally-determined near-field signal strength versus distance relationship (e.g. $1/d^6$) enables the magnitude of a given distance vector to be determined with accuracy. Accumulating signal strengths and corresponding (post-calibration) distances from all active channels, an acceptably self-consistent solution to tag location in a given grid relative to the witness antennas is determined. One witness antenna can be designated as the origin of a world coordinate system, and all subsequent distances determined from that point. This can be done for both implanted tag signals and signals from the emitters associated with a surgical tool.

In some embodiments, location data for the tag as well as for the emitters is used to provide indications to the surgeon of tag-medical device distance. In some embodiments, this information is presented in relative format, e.g. one or more visual indicators of tag direction relative to the tip of the medical device. It can also be more quantitative, e.g. a number of bars or lights corresponding to the number of centimeters between the tag and the medical device tip. In some embodiments, further use of the distance data is employed for rendering a simple image of the medical device and its relative orientation and distance to the tag.

The emitters associated with a medical device may comprise any feature that creates a detectable signal in a magnetic field. In some embodiments, the emitter is of the nature of any of the tags described herein. In some embodiments, coils mounted onto a surgical tool or otherwise used for calibration may be driven directly with a modulated version of the exciter signal from the activation device so that these coils serve as substitute tags and can be located by the receiver of the witness stations component in the same manner as an implanted tag. The modulation to drive these coils can be accomplished with a conventional switch or frequency mixer as modulator, or by numerical means via a digital synthesizer.

The component that contains the emitters may further comprise a display to assist the user in directing the medical device to the tag during a surgical procedure. In some such embodiments, a visual or audio display is provided on or associated with the medical device that receives location information about the tag from the computer system. The display may be one or more directional indicators such as LEDs, that indicate direction and/or distance to the tag. Color changes may be employed to indicate "on target" versus "off target" positions. In certain embodiments, the display comprises a first display for presenting distance to tag information (e.g., visual, audible, lights, color, vibration, tactile, etc.); a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the display comprises a plurality of displays (e.g., visual, audible, sensory, etc.) that allow the correct pitch and yaw axes to be employed (to minimize non-target tissue damage), and/or further a display that provides distance to tag information. In certain embodiments, a series of lights and/or sounds are provided on the display that guide the surgeon (e.g., the surgeon attempts to keep the lights in a center of an "X" series of lights, and/or to keep the volume of warning sounds off or as low as possible).

In some embodiments, an LED is employed for the display, and the LED is configured to emit light without the use of a power source (e.g., battery) within the tag. In some such embodiments, the two terminals (anode and cathode) of an LED are in contact with a coiled wire that, when in proximity to a changing magnetic field, induces a voltage and current into the coil, lighting the LED. The technology is not limited by the nature of the LED used. In some embodiments, the LED emits light in the visual spectrum. In some embodiments, the LED emits light in the ultraviolet or infrared spectrums. When a LED is switched on, electrons recombine with holes within the device, releasing energy in the form of photons. This effect is called electroluminescence and the color of the light (corresponding to the energy of the photon) is determined by the energy band gap of the semiconductor. In some embodiments, the LED comprises a lens or case (e.g., epoxy lens or case) surrounding a leadframe comprising an anvil and post. In some embodiments, the anvil comprises a semiconductor die in a reflective cavity and is connected to the post with a wire bond. The LED may be configured to produce different color effects (e.g., red, white, blue) (e.g., with $Y_3Al_5O_{12}$:Ce phosphor coating for white LED). In some embodiments, the semiconductor material is one or more of gallium arsenide, aluminum gallium arsenide, gallium arsenide phosphide, aluminum gallium indium phosphide, gallium (III) phosphide, indium gallium nitride, zinc selenide, silicon carbide (as a substrate), silicon (as a substrate), diamond, boron nitride, aluminum nitride, and aluminum gallium indium nitride. In some embodiments, the LED is a quantum dot LED. In some embodiments, the LED is a single-die LED to minimize its size profile.

The present disclosure is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

A patient previously identified as having a breast tumor is admitted to a medical facility. The patient is initially sent to radiology. The radiologist examines prior imaging information identifying the target tumor. The subject is administered a local anesthetic, usually lidocaine or a derivative, using a needle introduced percutaneously. The subject is positioned in an imaging device, generally either ultrasound, conventional mammography, or a stereotactic unit. The location of the tumor is determined. An introducer needle (usually 6-20 gauge) is inserted either into or just proximal to the tumor and a biopsy needle is placed through the introducer needle and a specimen is obtained using a variety of methods (suction, mechanical cutting, freezing to fix the position of the tissue followed by mechanical cutting). After the specimen is obtained and sent for pathologic examination, a 6-20 gauge tag delivery needle is inserted into the coaxial introducer needle to the tissue with the distal open end positioned at the lesion. A tag is inserted into the proximal end of the delivery needle and delivered by plunger through the opening at the distal end of the needle and into the tissue. Likewise, the tag could have been pre-positioned at the distal end of the delivery needle. Proper location of the tag is confirmed via imaging. The delivery needle is withdrawn, leaving the tag in place in the breast tissue.

This type of procedure can be performed in an analogous manner in virtually any body space, organ, or pathologic tissue with the intent of localizing that tissue or space for further diagnosis or treatment of any kind. Areas of particular interest include but are not limited to the following organs, and disease processes that take place within them: brain, skull, head and neck, thoracic cavity, lungs, heart, blood vessels, gastrointestinal structures, liver, spleen, pancreas, kidneys, retroperitoneum, lymph nodes, pelvis, bladder, genitourinary system, uterus, ovaries, and nerves.

In some embodiments, during surgery, the patient is placed onto an operating table with the surgical area exposed and sterilized. The surgeon is provided with the imaging information showing the location of the target tissue (e.g., tumor) and tag. An incision is made at the location of the entry point of the placement needle. The remote activating device is placed in proximity to the tissue to activate the tag. The detection component comprising the witness stations detects a signal from the tag and allows the surgeon to guide the direction medical device toward the tumor. Once the tumor is localized, the surgeon removes the appropriate tissue and, optionally, removes the tag.

In some embodiments, the system finds use in surgery with the tags placed as fiducials on or in the body. The relative position of the tags and any surgical instruments is located using the electromagnetic field. This information is communicated to a physician in real-time using a variety of methods including by not limited to visual (computer screens, direction and depth indicators using a variety of methods, haptic feedback, audio feedback, holograms, etc.), and the position of the instruments displayed on any medical images such as CT, Mill, or PET scans in 2D or 3D. This data finds use to guide the physician during a procedure, or is used as a training method so that physicians can perform a virtual procedure. Such system may be integrated into or provide alternative approaches to existing surgical systems, such as the STEALTH system (Medtronic) for applications such as neurosurgeries.

Further provided herein are systems, devices, assemblies, and methods for localization a tag in a tissue of a patient. For example, provided herein are systems, devices, and methods employing a detection component that is attached to or integrated with a surgical device, where the detection component can detect a signal from a tag in a patient, where the tag is activated by remote introduction of a magnetic field. In certain embodiments, the detection component comprises three sense coils arranged in a triangle.

Figure 7A:
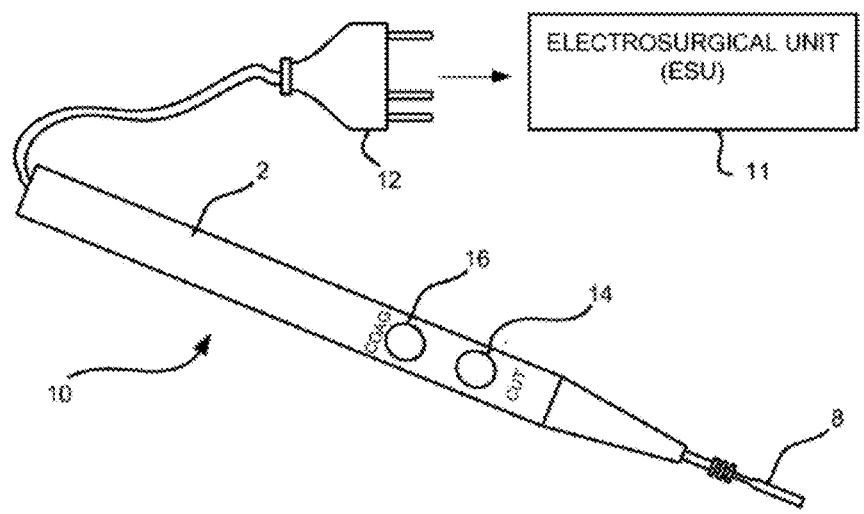
FIG. 7A shows an exemplary medical device (electrocautery device) from U.S. Pat. No. 8,998,899, which is herein incorporated by reference.
Figure 7B:
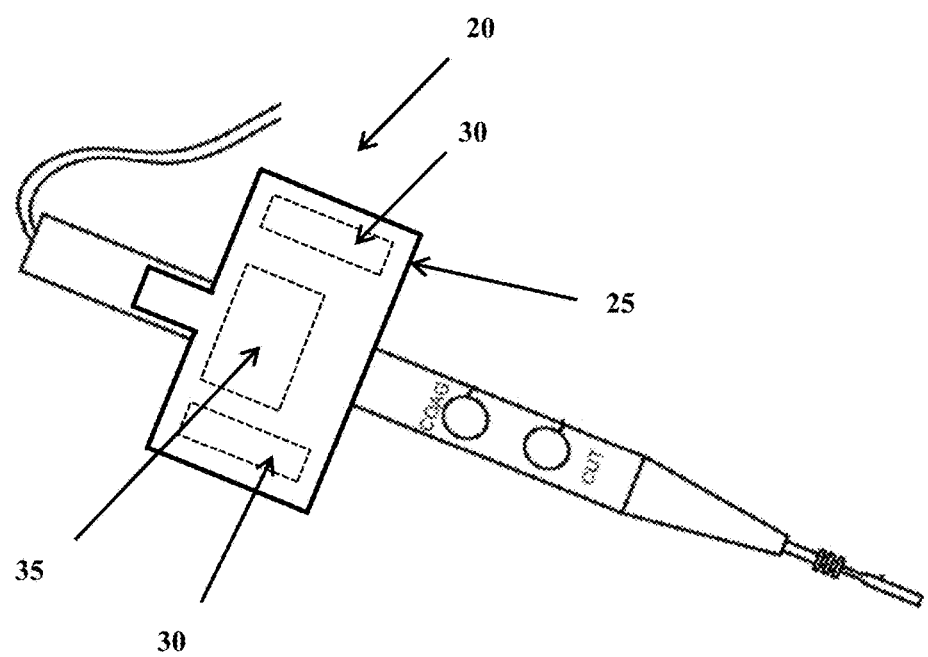
FIG. 7B shows an exemplary device/assembly of the present disclosure, showing a detection component attached to the medical device of FIG. 7A.

FIG. 7A shows an exemplary medical device (electrocautery device) from U.S. Pat. No. 8,998,899, which is herein incorporated by reference in its entirety. Specifically, FIG. 7B shows a surgical instrument (10), with a housing (2) having a coagulation button (16) and a cut mode button (14). The tip of the surgical instrument (10) is attached to electrode (8), that may be used for cutting and/or cauterizing tissue. The surgical device (10) is attached to an electrical surgical unit (11) via connector (12). The electrical surgical unit (11) provides power and various controls. FIG. 7B shows an exemplary device/assembly of the present disclosure, showing a detection component (20) attached to the medical device of FIG. 7A. The detection component (20) is shown with two sense coils (30) inside housing (25). Also inside the house (25) is electronics component (35) which may, for example, be used to process the signals received by sense coils (30), and/or provide a display to a user regarding distance to a tag embedded in a patient.

FIG. 6 shows an exemplary detection component (20) having a detection component housing (25) (e.g., composed of plastic or other material) which contains three sense coils (30) (which are arranged in a triangle configuration) and an electronics component (35). The housing (25) also has a device-securing opening (40) therein, which allows a medical device to be inserted and secured in place.

Figure 8:
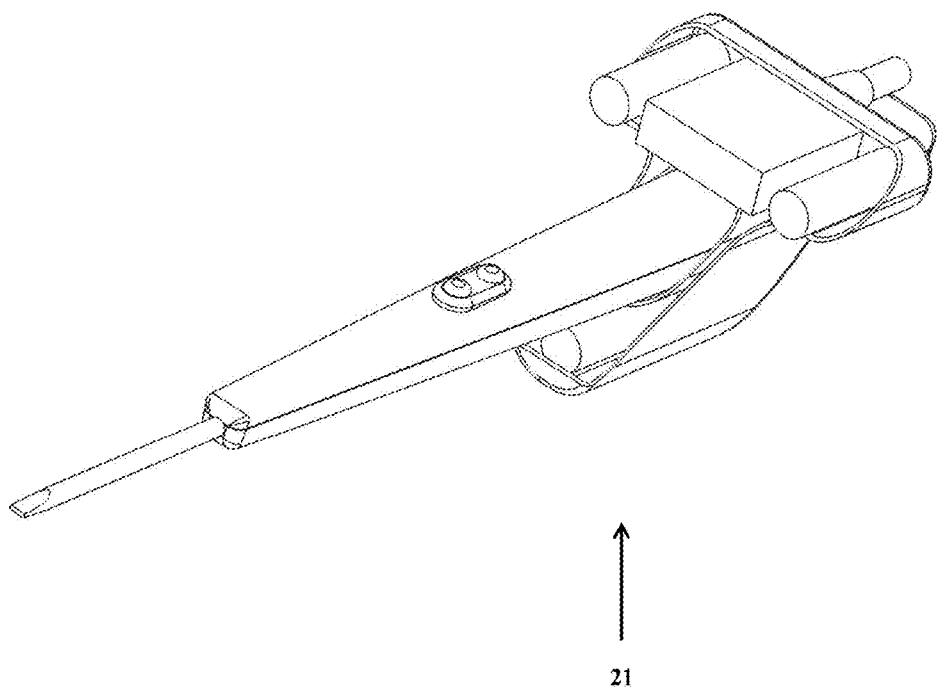
FIG. 8 shows an exemplary detection component—medical device assembly (21), wherein the surgical device is inserted through the device-securing opening of the detection component housing.

FIG. 8 shows an exemplary detection component—medical device assembly (21), wherein the surgical device is inserted through the device-securing opening of the detection component housing. In this assembly, for example, the detection component is positioned such that it does not interfere with a user (e.g., surgeon) using the medical device in its normal mode of use. In this figure, the detection component is positioned distal to the cutting and/or cauterizing end of the medical device, and away from the buttons used during operation.

Figure 9:
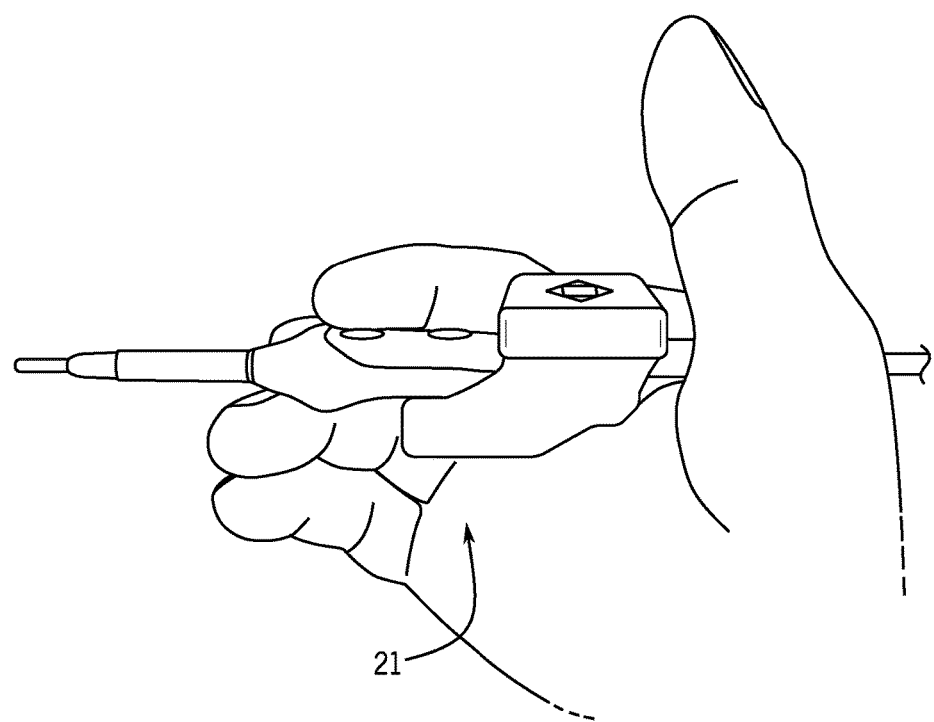
FIG. 9 shown a photograph of an exemplary detection component-medical device assembly.

FIG. 9 shown a photograph of an exemplary detection component-medical device assembly in the hand of a user. Again, the detection component is positioned such that the user is free to use the device and operate the buttons and cutting/cauterizing tip in a normal fashion.

Figure 10:
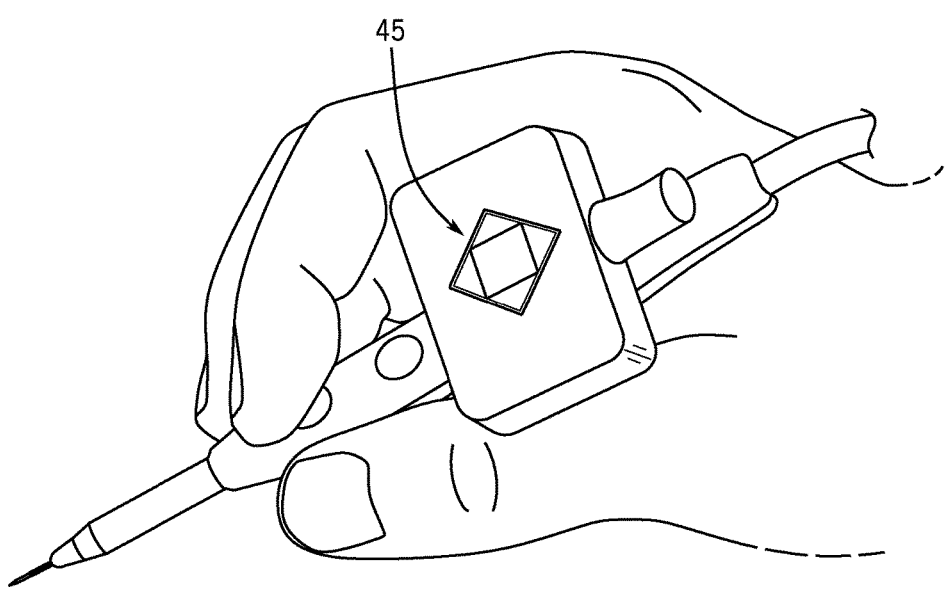
FIG. 10 shows a photograph of an exemplary detection component with a visual display (45) located therein.

FIG. 10 shows a photograph of an exemplary detection component with a visual display (45) located therein. A visual display may be used to inform the user (e.g., a surgeon) how far the tag (in the patient) is from the device, and may also be used to help keep the surgical device oriented in the correct planes (e.g., to avoid unnecessary cutting or cauterizing with the medical device). In certain embodiments, orientation and/or distance are indicated with a number of lights (e.g., 5 LED lights).

Figure 11:
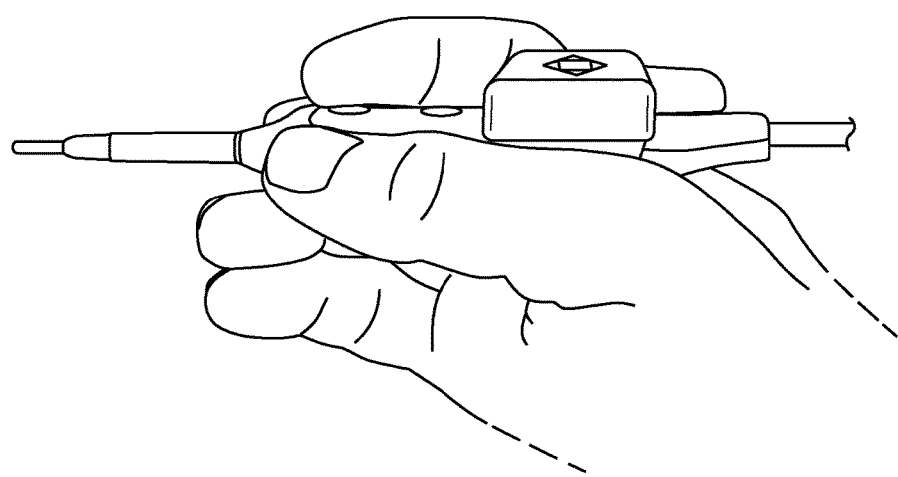
FIG. 11 shows a photograph of a side view of an exemplary detection component-medical device assembly.

FIG. 11 shows a photograph of a side view of an exemplary detection component-medical device assembly.

FIG. 4 shows a patient with a tag (100) inserted next to a solid tumor (110) (e.g., in breast tissue of the patient), wherein the patient is laying on top of a remote activating device (250), which is shown as a flat pad. Also shown is a surgical device (200), which, in some embodiments, is a detection component-surgical device assembly. The remote activating device may also be positioned closer to the tag (100) (e.g., by being placed on the abdomen), or placed further away (e.g., under the table or mattress the patient is supported on). In certain embodiments, the remote activating device (250) generates a magnetic field that passed through the patient's body, striking the tag, which causes a reflection or irregularity in the magnetic field. Such reflection or irregularity is detected by the detection component. A visual display (e.g., on the detection component or elsewhere) then reports the distance of the medical device tip (e.g., cutting and/or cautery tip) allowing the user (e.g., a surgeon) to precisely guide the medical device tip to the tumor. In certain embodiments, prior to any cutting of tissue, the detection component—medical device is moved all around the outside of the patient near the tag in order to calibrate the detection component.

Figure 5B:
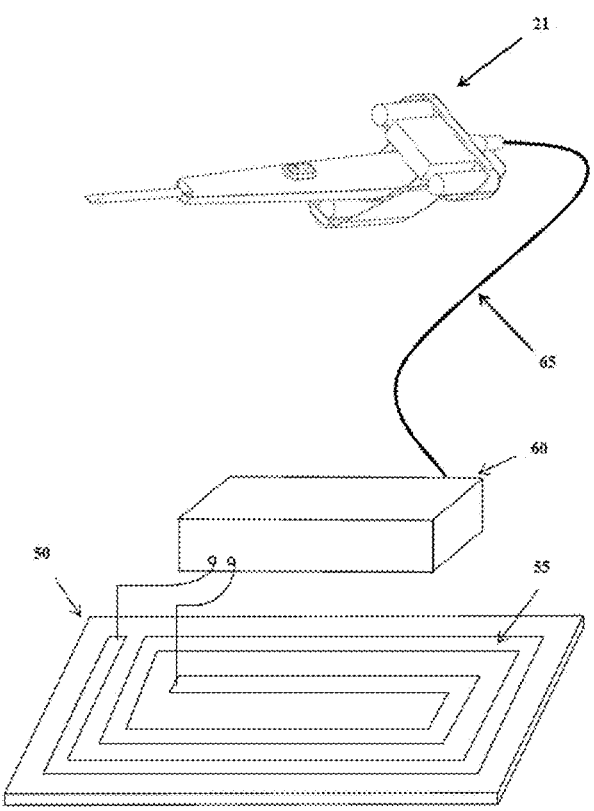
FIG. 5B shows a control unit (60) that is attached to both a remote activating device (50) and a detection component-medical device assembly (21). The remote activating device (50) has an excitation coil (55). The detection component—surgical device assembly (21) is attached to the control unit (60) via connection wire (65).

FIG. 5B shows a control unit (60) that is attached to both a remote activating device (50) and a detection component-medical device assembly (21). The remote activating device (50) has an excitation coil (55). The detection component—surgical device assembly (21) is attached to the control unit (60) via connection wire (65). In certain embodiments, when the power of the medical device is activated (e.g., to cut or cauterize) the control unit turns off the magnetic field from the remote activating device, and then turns the magnetic field back on when the power is not activated on the medical device. In this regard, any magnetic field generated by the medical device itself does not disturb the magnetic field generated by the remote activating device and vice versa. This help prevent the detection component from picking up false signals (from the medical device) that are not related to the location of the tag in the patient.

The technology is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

In certain embodiments, for surgical procedures, the patient is placed onto an operating table with the surgical area exposed and sterilized. The surgeon is provided with the imaging information showing the location of the tumor and tag. An incision is made at the location of the entry point of the placement needle. The remote activating device is placed in proximity to the tissue to activate the tag. The detection component detects a signal from the tag and allow the surgeon to guide the direction medical device toward the tumor. Once the tumor is localized, the surgeon removes the appropriate tissue and removes the tag.

Use of this system and procedure significantly reduces procedure cost, time, and patient inconvenience as compared to wire placement and other unguided surgeries. Use of the tag reduces the number of imaging steps required and reduces time spent in radiology and surgery. Further, the patient is not left waiting for surgery with a wire hanging out of their body. Avoidance of the wire further reduces pain or discomfort associated with the pulling on the wire.

In certain embodiments, the detection component is moved around the outside of the patient, sensing the tag at many different positions to build a 3D image of the location of tag within the tissue of the patient. Such data regarding the scan can, for example, be stored in the detection component or control unit and then used during a surgical procedure to determine the optimal point of entry into the patient's tissue, as well as the angle or angles which are best suited to approach the tag, and ultimately the associated tumor (e.g., to minimize cutting of non-target tissue and to maximize the removal of the tumor or tumors associated with the tag). Such 3D image scanning (e.g., prior to surgery) helps achieve the best result for the patient and helps reduce the need for repeating the procedure (e.g., to come back for parts of the tumor that were missed on the initial surgery).

In some embodiments, the 3D image generated by moving the detection component around the location of a tag in a patient is combined with an another image of the patient with the tag (e.g., generated by MRI, CT, etc.) to generate an image fusion. Combining two or more images of a patient using fiducials as marker points has been described previously (e.g., see, U.S. Pat. No. 7,848,553, and U.S. Pat. Pub. 20030153850, both of which are herein incorporated by reference in their entireties). Commercial image fusion systems include STEALTHSTATION system and PATH-FINDER system. Generating image fusions using a detection component described herein (e.g., where at least one or two implanted tags are used as fiducial points of reference), and then using the detection device for a procedure on a patient with the tags still in place, allows for real-time location correction for any movement of the patient (e.g., via breathing, changed position, organ movement during a packing procedure, etc.). In this regard, in some embodiments, the detection components herein, and their guidance system (e.g., audible, tactile, or visuals signals) is corrected during a surgical procedure (e.g., in real-time) so the operator is guided appropriately based on any changes in the patient tissue position (e.g., position of a tumor). The tag or tags serve as the fiducial points of reference for both the 3D image generated by the detection component, as well as the secondary image (e.g., from an MM or CT image). The tags also then serve as fiducial points of reference during the procedure to orient the detection device and account for changes in position of the patient. In some embodiments, the fiducials are implanted in a subject (e.g., in breast tissue) or be external (e.g., such as placed on each earlobe prior to brain scans and subsequent brain surgery using the detection component and corresponding surgical device). To see the position, in some embodiments, the tag is used in combination with one or more other fiducials. For example, one tag in the breast and a sticker containing a fiducial on each shoulder. This type of real-time use of image fusion and location information may be used in any type of suitable surgical or ablative procedure, including for example, neurosurgery, hepatobiliary surgery, gynecological surgery, ENT surgery, urological surgery, etc.

In certain embodiments, images (e.g., MRI, CT, etc.) that are generated for use with the detection component (and corresponding surgical device) are marked to indicate the location of a target tumor, including a surgical margin around the tumor to ensure complete removal. In some embodiments, a predetermined margin such as 0.5 . . . 1 cm . . . 1.5 cm . . . 2 cm etc., is set around a tumor to ensure removal. The surgical margin around a tumor could be set as a sphere, or drawn to correspond to any irregular shape of the tumor (e.g., hand drawn by a doctor on an image to match any irregular shape). In some embodiments, this surgical margin around a tumor is used such that, prior to using the detection component device and corresponding surgical device, one could calibrate for the signal intensity in the x, y and z axis related to this surgical margin such that whenever the device reaches a user defined boundary (the predetermined distance from the tumor) something changes, such as an audible, visual, or tactile signal (e.g., a yellow light when a user is at the surgical margin around tumor, and red light when the surgical device has gone within the predetermined surgical margin). In certain embodiments, there could be a signal warning that the surgical device is too close to the surgical margin (e.g., 5 mm), such as a red warning signal.

In certain embodiments, the tag is placed at or near the tip of the surgical instrument or device to track its location (e.g., whether fused with a medical image or not). For example, the tag could be placed on or near the tip of a nasogastric tube or bladder catheter to confirm the tip position from outside the patient. Such embodiments, may be used to improve safety of surgical procedures. Also, in some embodiments, the tag is placed on or near the tip of a vascular catheter, and the position of the catheter fused to a medical image (CT or MM) to give the location of the instrument in the human body. Likewise for any surgical instrument, catheter, endoscopic instrument, sensing device, biopsy needle, or anything else inserted into the human body where the tip location is important, a tag may be used near or at the tip of such devices. In certain embodiments, such as for simple applications, these could be unfused and the location determined from outside the body by a reader, or in the case of complicated anatomy, the location could be superimposed on a calibrated image set.

In certain embodiments, the detector component comprises one or more lasers that are directed onto (e.g. projected onto) the surgical/procedure field (e.g., internal tissue of a patient) as a guide to a the user (e.g., as a guide to the target tumor that is to be resected). In certain embodiments, multiple lasers are used (e.g., all the same color or providing different colors). Such laser projection onto the surgical/procedure field allows the user (e.g., physician) to be guided to the target (e.g., tumor) without the need to look away from the surgical or procedure field. In certain embodiments, the detection component is attached to a curved partially reflective lens that is, for example, be flipped up for easy viewing of the laser lights on the surgical field. Such a lens reflects the guiding lights towards the operator regardless of the orientation of the physician's head and the instrument surface. Such lens, in some embodiments, are used to decrease parallax, and improve the viewing angle for the physician.

In certain embodiments, the display for the detection component is not part of or attached to the detection component, and instead is remote. For example, the display component may be part of a head mounted, such as Google GLASS or similar devices that present a display close to a user's eye or eyes. In this regard, there may be a wireless connection between the detection component and the display, such as a BLUETOOTH connection.

In certain embodiments, to energize the implanted marker(s), a single large-diameter coil, in the remote activating device, can be located near the patient (e.g., beneath the patient), for example in the cushion or bedding that supports the patient on the operating table. This single exciter antenna will generally exhibit the strongest magnetic field in a direction normal to the table, and hence may not coincide with the axis of an implanted marker. In certain embodiments, to maximize the excitation of a marker with arbitrary location and orientation while limiting patient exposure to safe levels of magnetic field, it is desirable to have multiple solenoidal coils arranged in sub-arrays that are substantially orthogonal to each other (e.g., as shown in FIG. 13). In certain embodiments, these coils can further be subdivided into several shorter coils sharing the same axis, as shown in FIG. 12.

Figure 12:
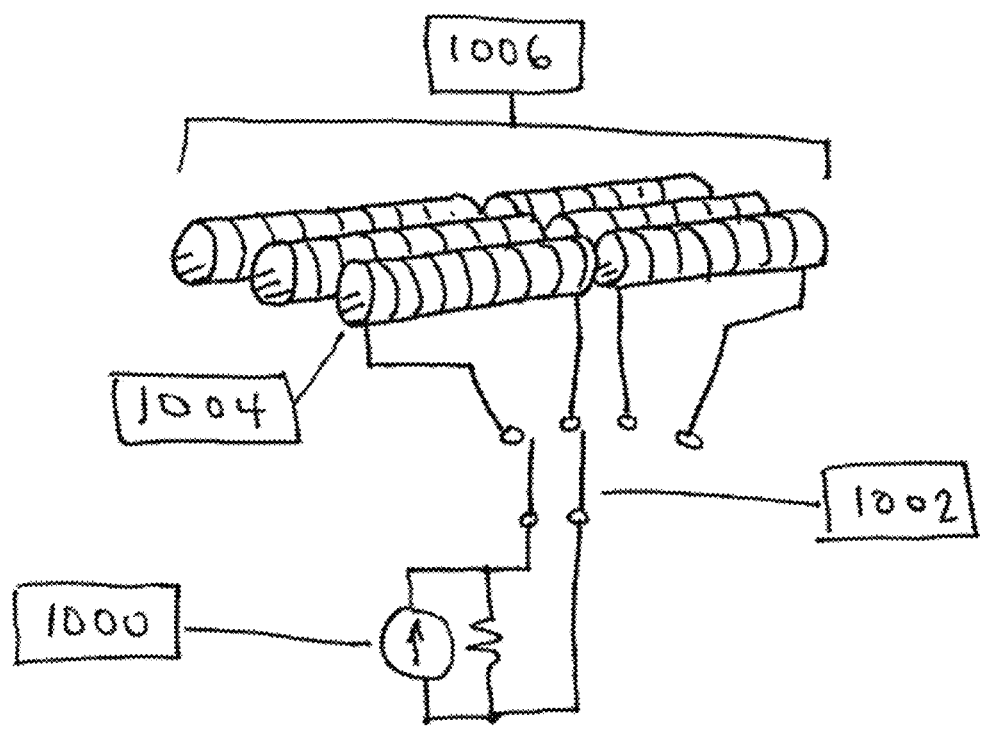
FIG. 12 shows an exemplary arrangement of one layer or sub-array of coils.
Figure 13:
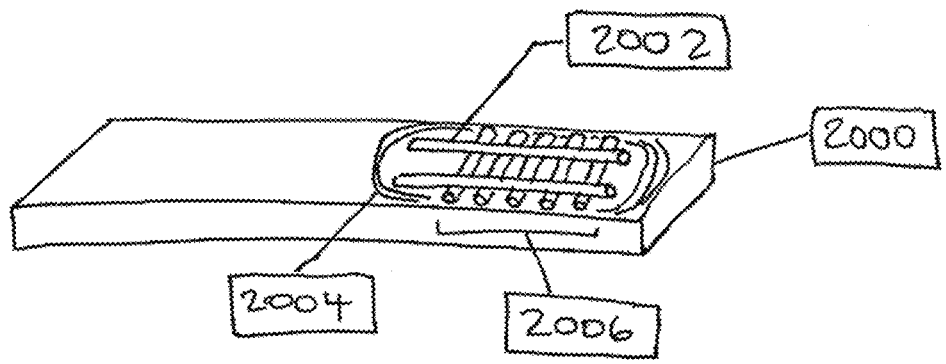
FIG. 13 shows an exemplary array of substantially orthogonal coils on or in a patient bed.

Exemplary subdivided coils are shown in FIG. 12. As depicted in this figure, a current source 1000 is used to drive an alternating current through one or more solenoidal coils 1004, which can be switched among these coils by switch

1002. For simplicity, only two coils are shown attached to the switch, and these coils are shown as independent, but it should be understood that some coils could be wired in series and that other switch or multiplexing techniques (including differential phasing or amplitudes of current sources) could be used to drive the array in a manner desired so that the implanted marker may be excited by a combination of coils, providing magnetic field to the marker while limiting the overall patient exposure to safe levels as determined by appropriate standards (e.g. IEEE). In additional embodiments, the spatial separation of these coils can be adjusted to enable a coarse localization of the marker with a given level of precision; while, in general, closer spacing would require more coils (but could help to locate the marker more precisely).

In certain embodiments, the exciter coils themselves are wound with magnet wire in one or more layers around a suitable core material, such as PVC, Teflon, or other low-loss and durable dielectric. In some embodiments, the core could be solid, hollow, or filled with a ferrite material, depending on the number of turns and value of inductance desired. These coils, in particular embodiments, would be of substantially similar inductances to facilitate resonant impedance matching to one or more current sources or generators 1000. In certain embodiments, the use of additional capacitors assists in making each coil resonant, which could broaden the range of acceptable inductance values for different coils in the array 1006.

As shown in FIG. 13, in certain embodiments, a set of sub-arrays of coils is arranged on a patient bed or cushion 2000. Longitudinal coils 2002 are arranged to approximately align with each breast, while a flat coil 2004 could encircle the orthogonal arrangement of longitudinal coils 2002 and lateral coils 2006. For simplicity, these coils are not shown as subdivided, but in some embodiments, they are composed of several co-linear coils, each of which is independently activated to energize the marker while limiting total magnetic field to safe exposure levels. In certain embodiments, the coils in FIG. 13 are embedded in cushion 2000, packaged in their own separate enclosure, or suspended underneath the patient bed or table if the table's material properties do not unduly influence the magnetic field from the coils.

We claim:

1. A system comprising:
   a) a tag, said tag comprising a radio-frequency identification (RFID) chip and an antenna, wherein said tag emits a sideband at a defined frequency, upon activation by a magnetic field;
   b) a remote activation device that generates a magnetic field within a region of the tag;
   c) a plurality of witness stations, each said witness station comprising an antenna configured to detect said sideband,
   d) a lock-in amplifier tuned to said defined frequency of said sideband; and
   e) a component that is attachable to a medical device, wherein said component comprises:
      i) at least two medical device location emitters, and
      ii) an indicator comprising a visual display that presents distance to tag information, and spatial orientation, for said medical device.

2. The system of claim 1, wherein said tag emits said sideband at a frequency defined by a number programmed into a counter in said RFID chip.

3. The system of claim 1, wherein said antenna of said tag comprises a coil antenna.

4. The system of claim 1, wherein said remote activation device comprises an excitation coil.

5. The system of claim 1, wherein said remote activation device comprises a pad configured to be placed in proximity to a patient having said tag embedded in said patient.

6. The system of claim 5, wherein said pad further comprises said plurality of witness stations.

7. The system of claim 1, wherein each witness station comprises a plurality of antennas.

8. The system of claim 7, wherein each of said witness station antennas feed a receiver channel that is time-division multiplexed.

9. The system of claim 7, wherein said plurality of antennas within at least one of said plurality of witness stations are arranged in an orthogonal manner to each other.

10. The system of claim 1, further comprising a computer system that receives information from said plurality of witness stations and generates information about a position of said tag.

11. A method of identifying a position of a tag, comprising:
   a) providing the system of claim 1;
   b) placing the tag in a human subject;
   c) generating a magnetic field with the activation device; and
   d) identifying a position of said tag in said subject by detecting said sideband emitted from said tag with said witness stations, and employing said lock-in amplifier.

12. The method of claim 11, wherein said position comprises relative location of said tag to said medical device.

13. The method of claim 11, wherein said position comprises distance of said tag to said medical device.

14. The system of claim 1, wherein said component comprises a sleeve that slips over a portion of said medical device.

15. The system of claim 1, wherein said medical device comprises an electrocautery device.

16. A system comprising:
   a) a tag, said tag comprising a radio-frequency identification (RFID) chip, wherein said tag emits a sideband at a defined frequency upon activation by a magnetic field;
   b) a component that is attachable to a medical device, wherein said component comprises:
      i) at least two medical device location emitters, and
      ii) an indicator comprising a visual display that presents distance to tag information, and spatial orientation, for said medical device;
   c) a remote activation device that generates a magnetic field within a region of the tag and the at least two medical device location emitters;
   d) a plurality of witness stations, each said witness station comprising an antenna configured to detect said sideband: i) emitted from said tag or changes in the magnetic field generated by said remote activation device in response to said tag; and ii) emitted from said at least two medical device location emitters or changes in the magnetic field generated by said remote activation device in response to said at least two medical location device emitters, and
   e) a lock-in amplifier tuned to said defined frequency of said sideband.

17. The system of claim 16, wherein said tag emits a sideband at a frequency defined by a number programmed into a counter in said RFID chip.

18. The system of claim 16, wherein said remote activation device comprises a pad configured to be placed under a patient having said tag embedded in said patient.

19. The system of claim 18, wherein said pad further comprises said plurality of witness stations.

20. The system of claim 16, wherein each of said at least two medical device location emitters comprises an antenna and emits a sideband at a defined frequency upon activation by the magnetic field.

21. The system of claim 16, wherein said at least two medical device location emitters are positioned to permit said plurality of witness stations to detect orientation of said medical device relative to said tag.

22. The system of claim 16, wherein said component comprises a sleeve that slips over a portion of said medical device.

23. The system of claim 16, wherein said medical device comprises an electrocautery device.

* * * * *